(12) United States Patent
Bini et al.

(10) Patent No.: US 10,709,458 B1
(45) Date of Patent: Jul. 14, 2020

(54) SURGICAL TOOLS AND METHOD FOR KINEMATIC ALIGNMENT

(71) Applicants: Stefano Bini, Piedmont, CA (US); Kenneth B Trauner, San Francisco, CA (US)

(72) Inventors: Stefano Bini, Piedmont, CA (US); Kenneth B Trauner, San Francisco, CA (US)

(73) Assignees: Stefano Bini, Piedmont, CA (US); Kenneth B. Trauner, San Francisco, CA (US)

( * ) Notice: Subject to any disclaimer, the term of this patent is extended or adjusted under 35 U.S.C. 154(b) by 333 days.

(21) Appl. No.: 15/294,443

(22) Filed: Oct. 14, 2016

Related U.S. Application Data

(63) Continuation-in-part of application No. 15/281,008, filed on Sep. 29, 2016, now Pat. No. 10,405,871.

(60) Provisional application No. 62/234,548, filed on Sep. 29, 2015.

(51) Int. Cl.
*A61B 17/15* (2006.01)
*A61F 2/30* (2006.01)

(52) U.S. Cl.
CPC .......... *A61B 17/154* (2013.01); *A61B 17/151* (2013.01); *A61B 17/155* (2013.01); *A61B 17/157* (2013.01); *A61F 2/30734* (2013.01)

(58) Field of Classification Search
CPC .... A61B 17/154; A61B 17/155; A61B 17/157
See application file for complete search history.

(56) References Cited

U.S. PATENT DOCUMENTS

| | | | |
|---|---|---|---|
| 2008/0275451 A1* | 11/2008 | McAllister | A61B 17/155 606/87 |
| 2009/0087276 A1* | 4/2009 | Rose | A61B 17/155 409/79 |
| 2018/0140440 A1* | 5/2018 | Jackson | A61B 17/157 |

* cited by examiner

*Primary Examiner* — Amy R Sipp
(74) *Attorney, Agent, or Firm* — Staniford Tomita LLP

(57) ABSTRACT

Tools and methods are used for aligned total knee arthroplasty (TKA) of anatomically or kinematically aligned knee. A block tool system references a distal femoral cut to provide a guide for the tibial cut. The block tool system can be used with the leg in full extension or in flexion. The block tools system includes a femur positioning block, an alignment arm coupled to the femur block, a femural cutting block, a tibial positioning block and a tibial cutting block.

4 Claims, 17 Drawing Sheets

US 10,709,458 B1

SURGICAL TOOLS AND METHOD FOR KINEMATIC ALIGNMENT

CROSS REFERENCE TO RELATED APPLICATIONS

This application is a continuation in part of U.S. patent application Ser. No. 15/281,008, "Surgical Tools And Method For Kinematic Alignment" filed on Sep. 29, 2016, which claims priority to U.S. Provisional Patent Application No. 62/234,548, "Surgical Tools And Method For Kinematic Alignment" filed on Sep. 29, 2015 which are incorporated by reference in their entirety.

BACKGROUND

Kinematic alignment is a new technique for performing total knee replacement. Currently over one million total knees are performed globally on an annual basis. Despite enormous advances in materials and technology, approximately 20% of knees have less than optimal outcome. The primary technical approach for knee replacement and for alignment of components is based on the theories proposed by John Insall in the 1970's and 1980s. This technique is based on creating mechanical alignment of the joint by "correcting" the joint line from an average 3 degrees of *varus* alignment relative to the tibial axis to a neutral (or perpendicular) alignment between the tibia and the tibial cut. The technique mandates creating asymmetric resection cuts of the femur and tibia to reorient the joint line and create equal flexion and extension gaps between the resected surfaces. The implants/components that are seated onto these bone cuts are thus forced to rotate around a non-anatomic axis. This creates soft tissue imbalance throughout the arc of motion that necessitates a series of soft tissue/ligament releases designed to re-establish balance in flexion and extension.

What is needed are newer techniques for performing total knee replacement that preserve the joint line of the pre-arthritic knee by creating symmetric resection cuts from the boney surfaces of the femur and tibia equal geometrically to the size of the implants to be used for reconstruction.

SUMMARY OF THE INVENTION

The present invention describes techniques tools and methods for more accurate and reproducible surgical performance of the anatomically or "kinematically" aligned knee. Key elements of this invention are designed to recreate the patient's unique anatomic joint line position in all three planes and thereby recreate anatomic ligamentous stability and kinematics. In different embodiments, the inventive process can include referencing the tibial cut from the distal femoral cut in full extension using the femoral cutting block/distal femoral cut (not the tibial axis) or in flexion. That is, the tibial cut is referenced from the femoral cut and in this invention this can be done in both flexion and extension.

In different embodiments, the inventive process can include the use of a distraction device to tension the ligaments prior to positioning the tibial cutting block/pins or a distraction wedge. The distraction device can be spreaders such as laminar spreaders or distraction blocks that are simply wedges of materials such as rubber, wood or metal that are designed to slip easily between the two matching surfaces of the femur and tibia and force them apart until appropriately tensioned. The distraction wedges can be ridged, have non slip surfaces or locking pins in various embodiments for the purpose of preventing motion once inserted. In different embodiments, the inventive process can include the use of hinged jigs that enable repositioning of the slot through which the saw blade passes without changing the position of the actual jig/cutting block. This can allow for rotation, flexion and extension adjustments.

DETAILED DESCRIPTION

Figure 1:
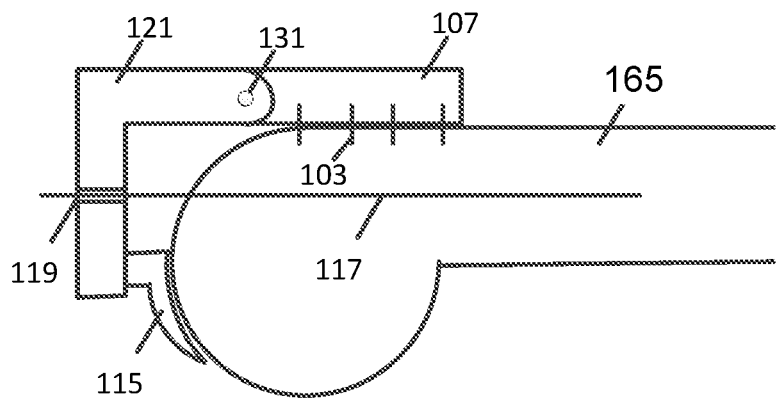
FIG. 1 illustrates a side view of an embodiment of block alignment system.

Recently a newer technique has been proposed for performing total knee replacement. This technique known as the "kinematic knee" alignment, or anatomic knee alignment, follows a set of principles that calls for preserving the joint line of the pre-arthritic knee by creating symmetric resection cuts from the boney surfaces of the femur and tibia that are equal geometrically to the size of the implants being used for reconstruction. This technique thus creates an anatomic reproduction of the pre-arthritic boney surfaces with tibial and femoral cuts that vary from the mean or average but reflect the individual patient's native anatomy. The implants/components that are seated onto these boney cuts will therefore rotate around the knee's native anatomic axis and the ligaments around the knee are therefore perfectly balanced throughout the arc of motion.

In mechanically aligned total knee arthroplasty (TKA) the surgeon cuts the distal femur and proximal tibia perpendicular to the femoral and tibial mechanical axes. These cuts change the angle and level of the natural joint line. A change in the natural angle and level of the joint line causes abnormal tightening or slackening of the collateral, retinacular, and posterior cruciate ligaments and abnormal kinematics. The undesirable consequences of abnormal kinematics are instability, motion loss, accelerated component wear, and component loosening from uneven load-sharing between compartments. In contrast, in kinematically-aligned TKA the surgeon cuts the distal femur and proximal tibia to restore the natural angle and level of the joint lines thereby minimizing these undesirable consequences.

Clinical data from limited centers have demonstrated promising results. Tools for the reproducible and consistent use of this technique by a surgeon new to the technique however are lacking. This invention describes numerous novel tools and methods for accurate and reproducible production of anatomic alignment in total knee arthroplasty.

Accurate kinematic or anatomic alignment of the Femoral and Tibial components of the Total Knee Replacement can include various devices and techniques. In a first embodiment, a kinematically-aligned TKA can include some or all of the following process steps and tools/instruments.

Femur

A distal end of a femur can be cut while the leg is in flexion. The thickness of the resection cut of the distal end of the femur can be determined in a number of ways as can the angle of the cut relative to the femoral axis. If a cut is inaccurate, this can result in errors in component placement. For example, removing too much bone can result in over resection and not removing enough bone can result in under resection of the bone which in turn places the component in the wrong position. Finding the correct resection level of the bone may be challenging in very large or very small femurs. For example, in average sized femurs, the typical flat plate of the standard instrument sizing guides will be accurate. However, in a large femur the resection guide can be too short to contact the most distal surface of the femur and may ride proximal to the correct resection point. Further, both the position of the cutting block in the anterior posterior plane relative to the femoral axis may also change the position of the cut.

In an embodiment of the invention an adaptable shim can be used to alleviate these problems. Accurate determination of the distal most point of the femur can include using a cupped adaptable shim that attaches to existing cutting blocks and which can correctly position the cutting block to match the anatomy of the distal femur and make up for lost cartilage or bone which may be worn away from wear. With reference to FIG. 1, an alignment tool can include a femur block 107 and an alignment arm 121, which can be coupled by a releasable and rotatable coupling 131. An intra-medullary (IM) rod 117 can be placed in the femur 165 and a portion of the IM rod 117 can extend out of the proximal end of the femur 165. An alignment assembly which can include a femur block 107 and an alignment arm 121 coupled to a cupped reference 115 can be placed on the proximal end of the femur 165. In this example, the alignment arm 121 can also have an IM rod hole 119. The arm can be positioned on the femur 165 with a concave surface of the cupped reference 115 against the proximal end of the femur 165 and the IM rod 117 positioned through the IM rod hole 119. This can provide an axial position reference for the femur block 107 which can then be attached to the femur 165 with a plurality of pins 103. The femur block 107 can have several sharp ridges and/or protrusions which are pressed against the femur 165 and hold the femur block 107 steady while the pins 103 are being placed. Alternatively, pins 103 can be supplied with sharp cutting tips that are easily pressed into the femur 165.

Figure 2:
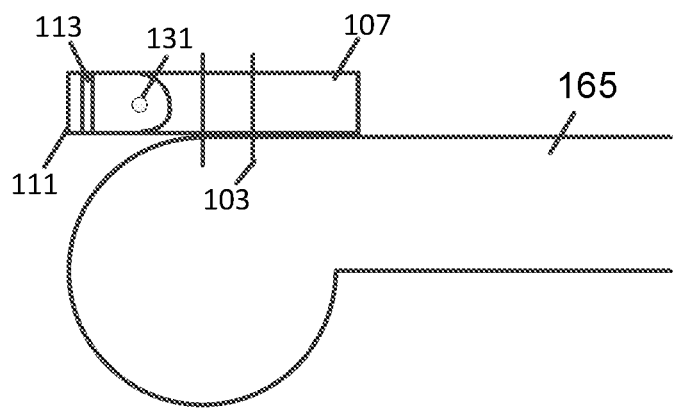
FIG. 2 illustrates a side view of an embodiment of a cutting block system.
Figure 3:
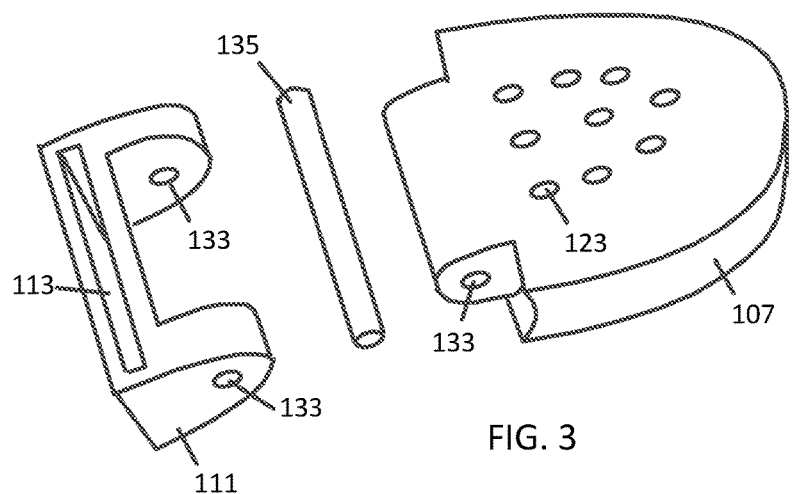
FIG. 3 illustrates a top perspective view of an embodiment of a cutting block system.

With reference to FIG. 2, once the femur block 107 is attached to the femur 165, the arm can be removed from the femur block 107 and a cutting block 111 can be attached with a rotatable coupling 131 to the femur block 107. The cutting block 111 can include a blade slot 113 which can provide an alignment slot for a cutting blade to cut a proximal portion of the femur 165. The femur block 107 can be used to position and attach a cutting block positioner 111 on the femur 165 in order to accurately cut the femur. FIG. 3 illustrates a top perspective view of the cutting block 111 and the femur block 107. In this embodiment, the cutting block 111 can be coupled to the femur block 107 with a coupling rod 135 that is placed through the rotational coupling holes 133 in the cutting block 111 and the femur block 107. The coupling rod 135 can be removed from the femur block 107 when the tool components need to be changed. The femur block 107 can include a plurality of pin holes 123.

Figure 4:
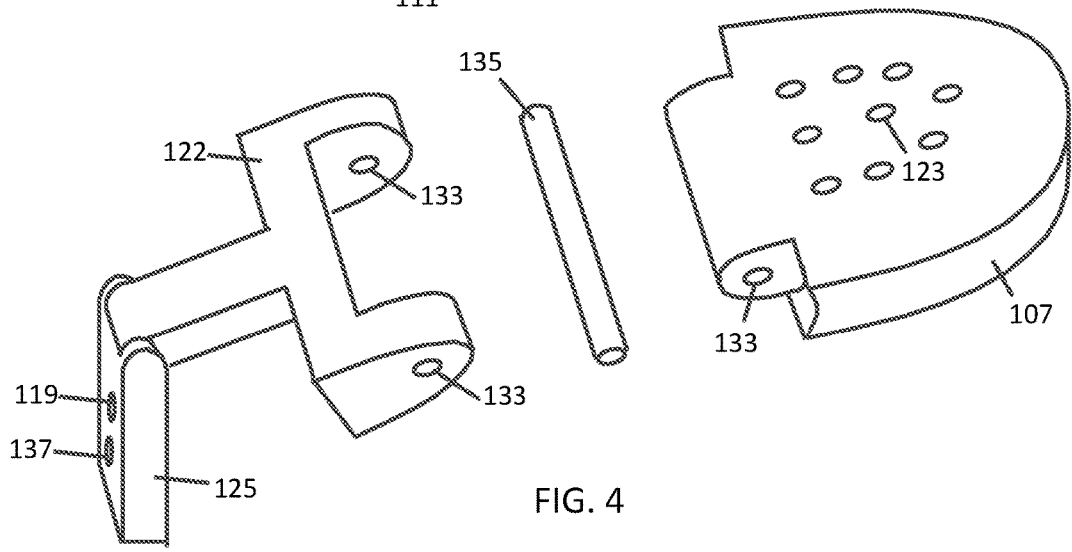
FIGS. 4 and 5 illustrate top perspective views of an embodiment of a block alignment system.

FIG. 4 illustrates an exploded perspective view of femur block 107, a coupling rod 135, an alignment arm 121 and a second rotational arm 125. The alignment arm 121 can be rotatably coupled to the femur block 107 with the coupling rod 135 placed through the coupling holes 133. A secondary arm 125 can be coupled and rotated relative to the rotational arm 122. The axis of rotation of the secondary arm 125 can be parallel to the axis of rotation between the femur block 107 and the rotational arm 122. An alignment shim can be coupled to the secondary arm 125 at the mounting hole 137. The secondary arm 125 can also include an IM rod hole 119 and one or more mounting holes 137 or coupling features. The secondary arm 125 can rotate to a 90 degree orientation relative to the rotational arm 122 and the IM rod hole 119 can be placed around the IM rod in the proximal end of the femur, similar to the configuration shown in FIG. 1.

Figure 5:
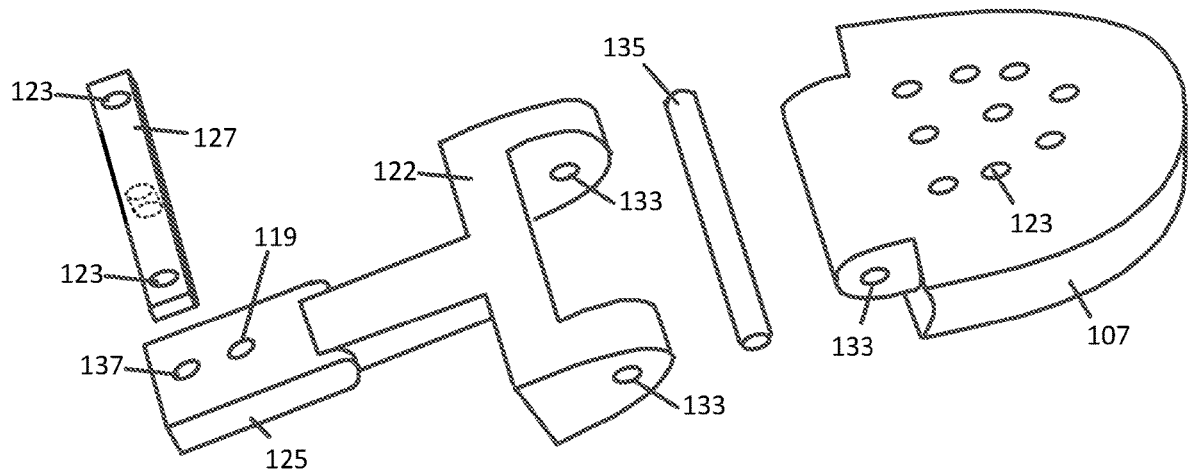

With reference to FIG. 5, the rotational arm 122 can be planar and aligned with the second rotational arm 125. In this embodiment, a guide 127 can be coupled to the second rotational arm 125. The guide 127 can include one or more guide holes for pins that can be driven into a distal end of a femur or a proximal end of the femur. Although the cutting alignment tools have been described as being used on the distal end of the femur, in other embodiments the inventive system and methods can also be used on the proximal end of the femur.

Internal Rotation

Femoral component rotation in kinematic alignment is determined by the posterior condylar axis. The standard "paddles" used by the existing sizing guides can work for most but not all femurs because frequently the paddles are either too narrow (medial to lateral plane) or not deep enough in the Anterior to Posterior (AP) plane to reach (and reference from) the distal most aspect of the posterior femoral condyles of the femur. In an embodiment a solution would include an insert that creates a deeper or wider footprint for the sizing guide, i.e.: depth/length of and distance between the paddles. In an embodiment the insert or extension can be attached to the paddle through a curved capture guide that slips around and cups the femoral condyle. Since the shape of the femur (radius of curvature) is generally identical for both the distal and the posterior condyles, the same cup shape can be used for the distal femur and the posterior femoral resection guides. In different embodiments posterior guides will also allow +/−1 and 2 mm resection accuracy.

Skived Cut

In different embodiments there can be a problem where the saw blade tends to flex and under-resect in areas of dense sclerotic bone. A better or tighter resection mechanism can be indicated. Various methods can be implemented to improve the cut accuracy including: a deeper saw capture guide slots to prevent saw flexion; and/or stiffer pin construct to prevent the block from extending or flexing during resection. In some embodiments, a new distal block or an attachment can be used to improve the saw capture's ability to drive the saw blade.

Distal Femoral Cutting Block Resection Angle

The flex, extension, as well as rotation of a knee can be changed if the pin used to lock the cutting block in place moves as the locking pins are inserted. The pins can have a tendency to be positioned over a sloped surface and have trouble getting a hold on the bone, and skive until they catch. This can change the position of the cutting block by several degrees. In an embodiment with reference to FIG. 1, an alignment arm 121 may have an IM rod hole 119 that is designed to slide over the IM rod 117. The attached block 107, unlike most blocks, may need to be adjustable even after being pinned. The entire block 107 can slide over the Intra-Medullary (IM) rod 117. The bone contact surface of the block 107 can have spikes/ridges can grip the bone and prevent the block 107 from slipping. Pins 103 with cutting tips can also help to prevent slipping. If resection is less than expected, the IM rod 117 can be readjusted to allow for more rotation (Varus valgus) without removing the pins 103 (see technique guide). Adjustment can allow for concise changes such as one degree/one mm increments.

Tibia Cuts

A proximal cut to the tibia can be a challenging cut as there are few reference points that are reliable in an arthritic knee if one wants to do an anatomically correct cut that restores the pre-arthritic position of the tibial plateau. Except in severe deformity the anterior and posterior cortical rims are still present whereas the lateral or medial rims may not be.

Height: The inventive method can determine how much to resect if there is a lot of bone loss so that the resection is an equal amount of bone medially and laterally. In extension the distal cut should be parallel to the tibial cut whereas in flexion, due to slight relative Internal femoral rotation the gap should be wider laterally than medially by about 2-3 mm.

Rotation: the true bisector for the rotational plane is important since the system is applied to an anatomic posterior slope with a goal of matching the axis to that of the tibial spine and also the patient's normal, standing anatomy.

Slope: the goal is an anatomic posterior slope, as visualized from the side of the medial arthrotomy. However, if the bone that is resected clearly shows inadequate slope or unequal medial lateral medial/lateral resection, the block may need to be adjusted, adjustable or a recut block should be available.

Sizing: the block is intended to provide cortical support of the tibial plate.

Patella Cut

The patellar cut angle should be perpendicular to the axis of the patella in two planes, centered on the ridge of the patella, which is in line with the patellar nose. Amount: equal to the thickness of the patella. Tracking: should match the femur perfectly with no tilt.

In different embodiments, the inventive process can include the use of curved surfaces rather than flat surfaces as a means by which to identify the reference point from which to measure the resection point on the distal femur. In different embodiments, the inventive process can include the ability to re-align the resection block following the initial cut (if deemed inappropriate) without moving the pins used to secure the cutting block to the femur or tibia. Three different method options will be outlined: one in which the native/original cutting blocks that come with any given, existing instrument set are adapted by means of a shim/attachment to better enable kinematic alignment cuts, and secondly the design of single or multi-use cutting blocks that create the distal femoral cut and the proximal tibial cut. These blocks come in two versions: one allows cutting the tibia in flexion, the other in extension and both reference the tibial cut from the femoral cuts. This is to be done through the placement of pin holes in the cutting block that enable the block to be repositioned in both rotational planes (varus/valgus) and (longitudinal planes) proximal to distal without changing the pins.

Femoral Distal Cuts

Figure 6:
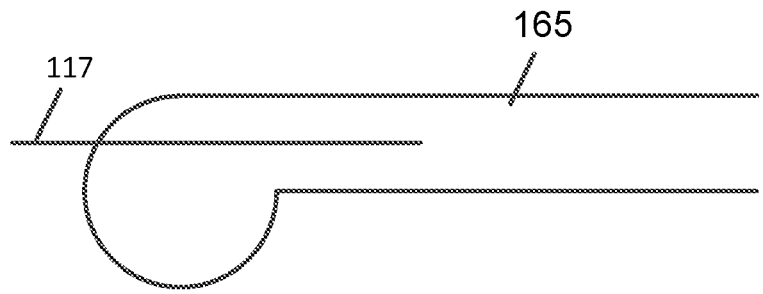
FIGS. 6-8 illustrate side views of an embodiment of a block alignment system.
Figure 7:
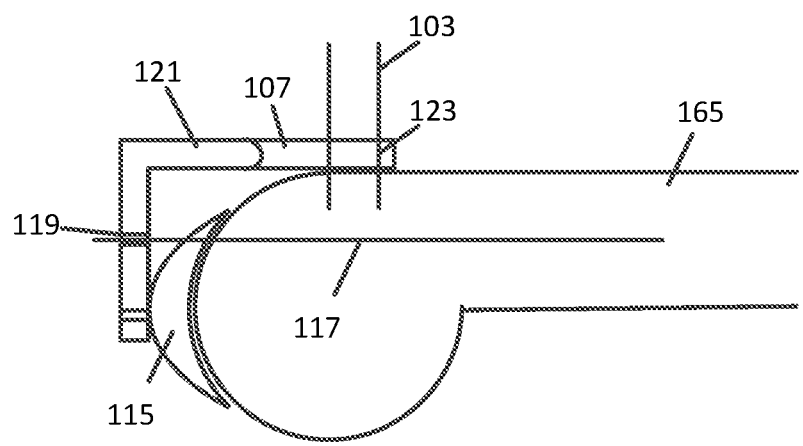
Figure 8:
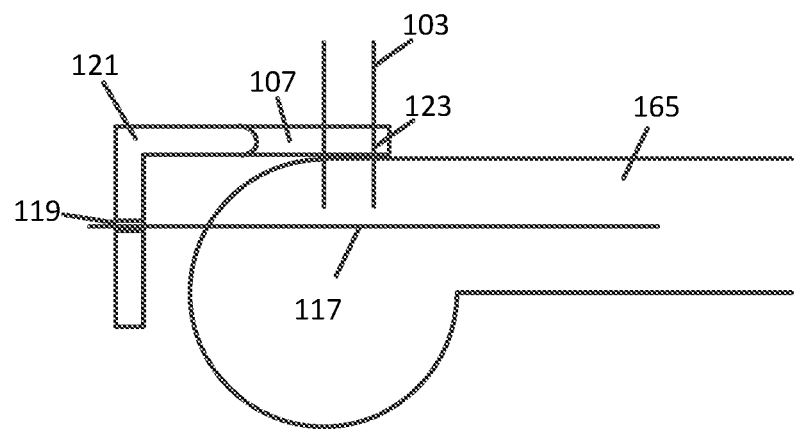
Figure 9:
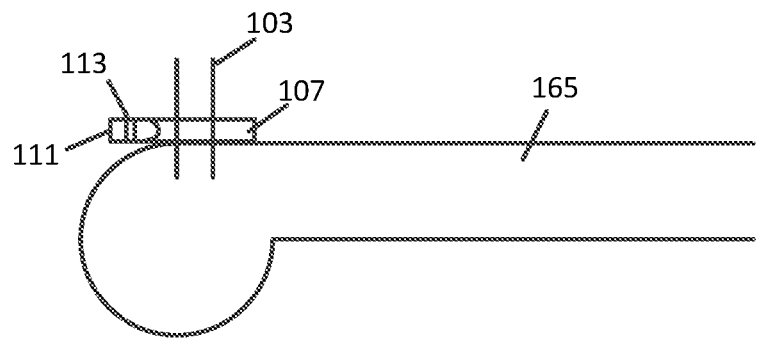
FIGS. 9 and 10 illustrate side views of an embodiment of a cutting block system.
Figure 10:
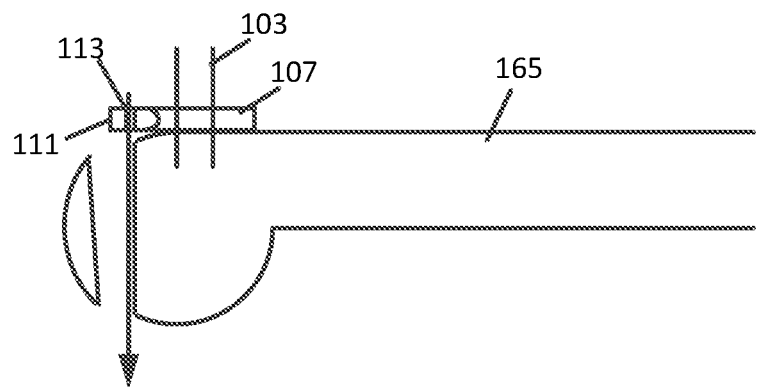

FIGS. 6-9 illustrate an embodiment of a surgical sequence using a novel femoral cutting block but many of the native instruments. When only using shims to adjust the cut using native instruments, the shims can be attached to the native cutting block. With reference to FIG. 6, an IM rod 117 is placed in the distal end of the femur 165. The IM rod 117 can be aligned with the center axis of the femur 165. With reference to FIG. 7, a cupped reference 115 can be attached to the alignment arm 121, which is coupled to the femur block 107. The IM rod hole 119 can be placed over the IM rod 117 and the cupped reference 115 can be placed against the end of the femur 165. With the proper positioning of the alignment arm 121, the femur block 107 can be placed against the femur 165 and pins 103 can be placed through pin holes 123 to secure the femur block 107 to the femur 165. With reference to FIG. 7, the femur block 107 can be secured to the femur 165 and the cupped reference 115 can be removed. With reference to FIG. 9, the alignment arm has been removed and the cutting block 111 is attached to the femur block 107. The blade slot 113 defines a cutting plane that will be cut from the femur 165. With reference to FIG. 10, a blade is placed through the blade slot 113 and the proximal end of the femur 165 is cut away.

In an embodiment, an adaptable shim allows surgeons to accurately determine the distal most point of the femur. A cupped adaptable shim can be attached to existing cutting blocks. The cupped adaptable shim can conform to the geometry of the distal end of the femur. The shims can be designed to fit onto the native/original cutting blocks. The locking clip mechanism may therefore differ for each different system it is designed to work with.

In an embodiment, cupped shims can be used with the inventive process and attached to the alignment arm 121 shown in FIG. 8. In different embodiments cupped shims can be symmetric or asymmetric such as: spherical, oblong and rectangular. The cupped shims can be flexible structures with non-uniform thicknesses. For example, the cupped shims can be thicker at a center portion where the shim contacts the bone. The cupped shims can be thinner at the outer edges to match multiple radiuses of curvature. The cupped shims can have a smooth concave inner radius as well as radial fenestrations that can improve the flexibility and adaptability of the shim. The fenestrations can be symmetric, non uniform and/or nonlinear. The fenestrations can be distributed across the shims. The thicknesses of the fenestrations can also be variable. For example, in different embodiments the fenestrations can be thinner at the outer edges and widths of the cuts and thicker at the inner edges. The fenestrations can be adapted to right/left to conform to curvature of condyles. With these features, the shim can adapt to the shape of the patient's femur. The shim can have a coupling to the cutting block and alignment arm that can also be rigid where the shim is coupled to the cutting block. In some embodiments, the apparatus can include a shorter anterior flange and a longer posterior flange.

The cupped shims can provide free rotational freedom at junction to allow the component to conform as necessary. The shims can be free to slide from the medial to lateral portion. The shim may be made of plastic or rubber or metal or any other suitable material. The shim may be made in multiple sizes to match various radii of curvature of the patients' femurs.

In different embodiments, various different types of shims can be attached to the alignment arms. The most appropriate shim can depend upon the patient's anatomy and the bone cutting that is being performed. The cupped and adaptable shim can allow a surgeon to decrease the amount of bone resected by one, two or three mm depending on the amount of distal surface lost. Examples of different shims are illustrated in FIGS. 16-31.

Figure 18:
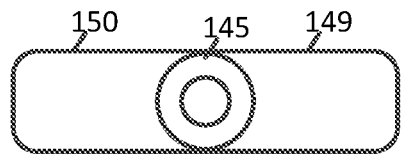
FIG. 18 illustrates a top view of a symmetric cup shaped alignment shim.
Figure 19:
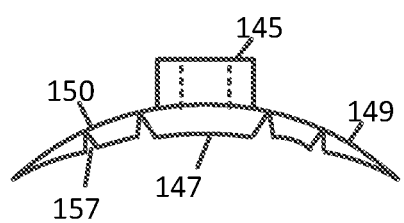
FIG. 19 illustrates a side view of a symmetric cup shaped alignment shim.

FIG. 18 illustrates a top view of an embodiment of a first rectangular shim 149 and FIG. 19 illustrates a side view of the first rectangular shim 149. The first shim 149 has a tapered body that is thicker in the center and thinner at the ends of the legs 150. The lower concave surface 147 can include one or more slots 157 which can extend partially through the thickness of the first shim 149 and function to increase the flexibility of the legs 150 of the first shim 149. In this embodiment, the first shim 149 is an elongated rectangular structure that has two legs 150 that are symmetric about the connection coupling 145. The first shim 149 can be attached at the coupling 145 to the alignment arm.

Figure 20:
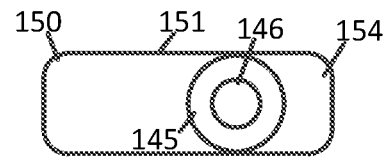
FIG. 20 illustrates a top view of an asymmetric cup shaped alignment shim.
Figure 21:
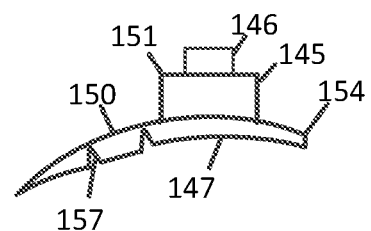
FIG. 21 illustrates a side view of an asymmetric cup shaped alignment shim.

FIG. 20 illustrates a top view of an embodiment of a second rectangular shim 151 and FIG. 21 illustrates a side view of the second rectangular shim 151. The second shim 151 also has a lower concave surface 147 and is rectangular in shape. However, the structure has asymmetric legs 150, 154. In this example, the first leg 150 is longer than the second leg 154 from the connection coupling 145. The connection coupling includes a cylindrical rod 146 which can fit within the hole in the alignment arm. In an embodiment, the rod 146 and the hole in the alignment arm can have corresponding grooves which can help to hold the rod 145 within the hole and prevent rotation.

Figure 22:
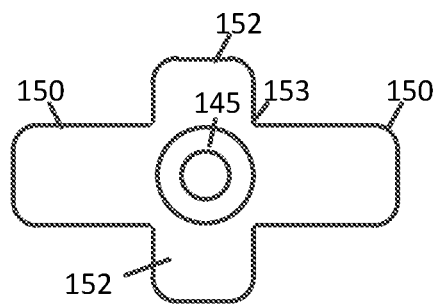
FIG. 22 illustrates a top view of a symmetric cross cup shaped alignment shim.
Figure 24:
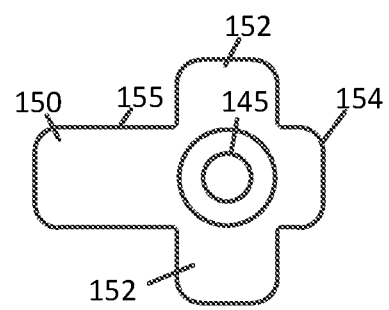
FIG. 24 illustrates a top view of an asymmetric cross cup shaped alignment shim.
Figure 23:
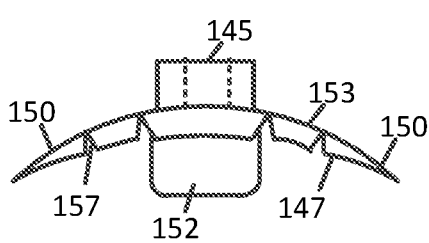
FIG. 23 illustrates a side view of a symmetric cross cup shaped alignment shim.
Figure 25:
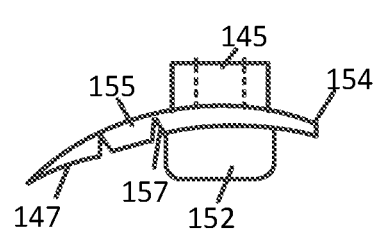
FIG. 25 illustrates a side view of an asymmetric cross cup shaped alignment shim.

FIG. 22 illustrates a top view of an embodiment of a third shim 153 and FIG. 23 illustrates a side view of the third shim 153 which has a symmetric cross shape with a rectangular body and side legs 152 that can be perpendicular to the main body and symmetric about the connection coupling 145. Both the main legs 150 and the side legs 152 have lower concave surfaces 147. The main legs 150 and side legs 152 allow the shim 153 to be positioned on a three dimensional round surface in order to prevent movement off of the curved bone surface. FIG. 24 illustrates a top view of an embodiment of a fourth shim 155 and FIG. 25 illustrates a side view of the fourth shim 155 which has an asymmetric cross shape with a long leg 150, a shorter leg 154 and side legs 152 that can be perpendicular to the long leg 150 and a shorter leg 154.

Figure 26:
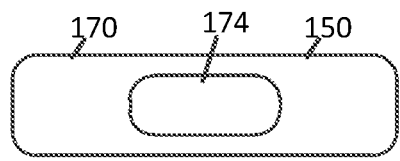
FIG. 26 illustrates a top view of an alignment shim with adhesive coupling.
Figure 28:
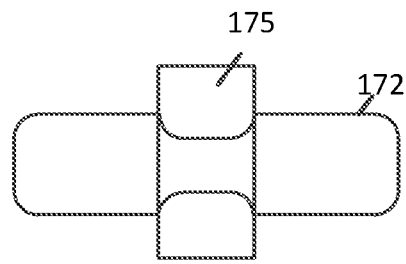
FIG. 28 illustrates a top view of an alignment shim with clip coupling.
Figure 27:
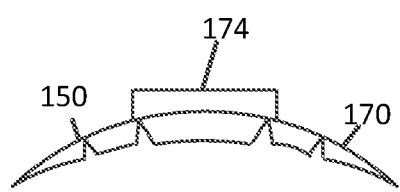
FIG. 27 illustrates a side view of an alignment shim with adhesive coupling.
Figure 29:
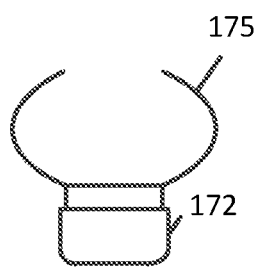
FIG. 29 illustrates a side view of an alignment shim with clip coupling.

In different embodiments, various types of coupling mechanisms can be used to attach the shims to the alignment arms. FIG. 26 illustrates a top view of a fifth shim 170 and 27 illustrates a top view of the fifth shim 170 which is similar to the first shim shown in FIGS. 18 and 19. However, the shim 170 includes an adhesive coupling 174, which is coupled to the alignment arm. FIG. 28 illustrates a top view of a sixth shim 170 and FIG. 27 illustrates a front view of the sixth shim 170 which includes a round clip 175. In this embodiment, the clip 175 is used to attach the sixth shim 172 to the alignment arm.

Figure 16:
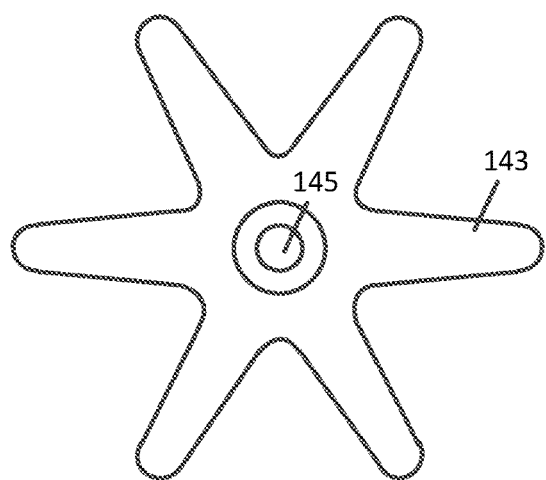
FIG. 16 illustrates a top view of a star shaped alignment shim.
Figure 17:
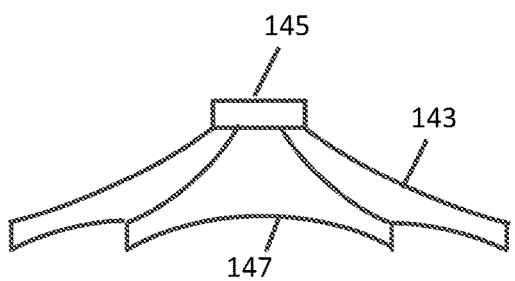
FIG. 17 illustrates a side view of a star shaped alignment shim.

In other embodiments, the shims can have different shapes. For example, FIG. 16 illustrates a top view and FIG. 17 illustrates a side view of a star shaped reference shim 143 which can be attached to the alignment arm at a coupling 145. The star shim 143 can have a plurality of legs that extend outward from the center and the lower surface, which can be placed against the tibia and can be concave. This star shim 143 can be appropriate when used with a sympatric proximal tibia end surface.

Figure 30:
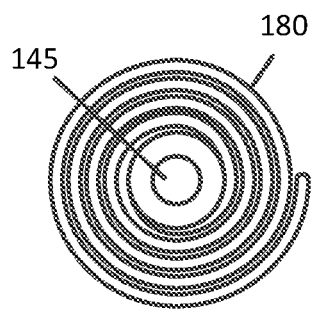
FIG. 30 illustrates a top view of a spiral shaped alignment shim.
Figure 31:
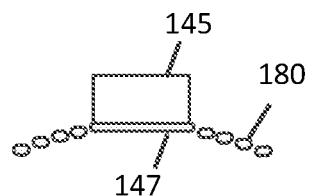
FIG. 31 illustrates a side view of a spiral shaped alignment shim.

FIG. 30 illustrates a top view of a spiral shim 180 and FIG. 31 illustrates a side view of the spiral shim 180 which has a concave lower surface 147. Like the other shims, the concave lower surface 147 can be placed on a round bone surface and the coupling 145 can be attached to the alignment arm.

In some embodiments, the shims may need to allow the blade to pass without being hit by the blade anteriorly but posteriorly the blade can be longer and serve as a way to create an end point to the saw. The cup material can be: plastic or rubber or any other suitable material. The pins holding the distal femoral cutting block to the femur can prevent the block from being rocked into flexion/extension during pin placement and/or resection/cutting.

In some embodiments the described shims can be used in different configurations. For example, there can be situations during TKA where the bone resected is thicker than what was expected/wanted. In this situation, a shim can be attached to the back of the 4 in 1 block. The 4 in 1 block is a metal block with 4 cutting slots which are fixed to the femur following the distal femoral cut and is used to make four chamfers in the bone. Most manufacturers use a variation of this instrument as part of their surgical instrumentation. The shim can make the block sit proud of the distal femoral cut. In so doing, the chamfer cuts will be higher by 1-2 mm and thus prevent the femoral component from seating all the way to the distal cut. This insert or shim could be held in place using a sticky surface that attaches to the back of the 4 in 1 cutting block on the over-resected side.
Femoral Cutting Block Option.

Figure 11:
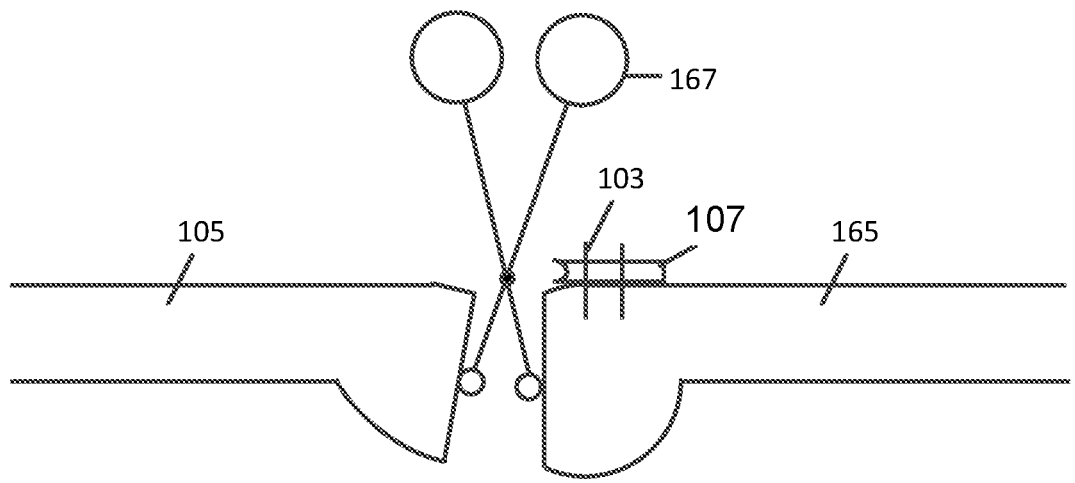
FIGS. 11-15 illustrate side views of an embodiment of a tibia cutting block system.
Figure 12:
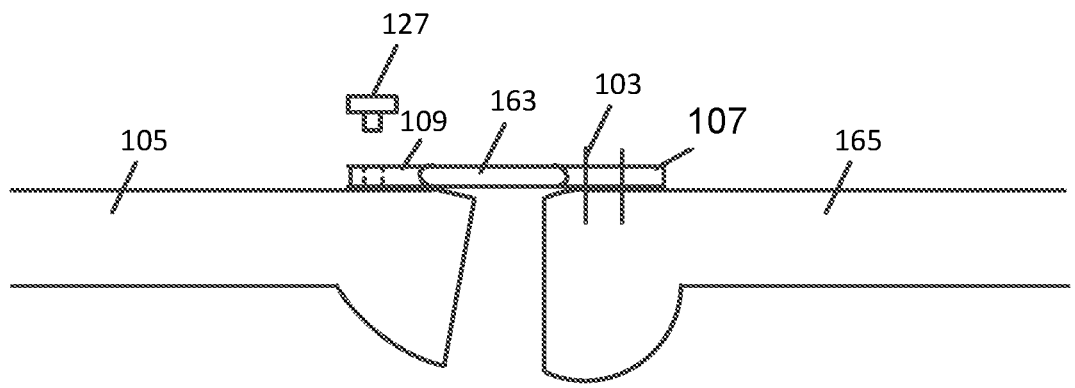
Figure 13:
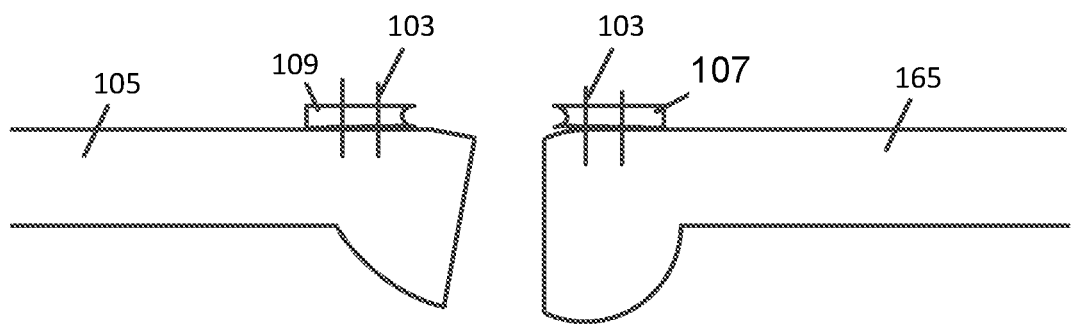
Figure 14:
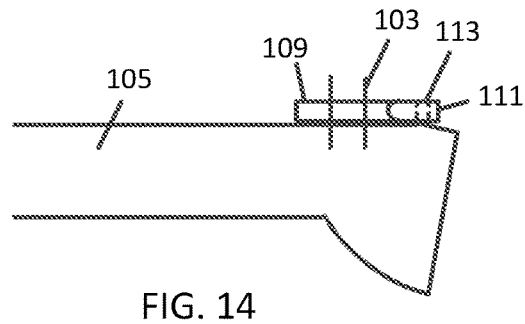
Figure 15:
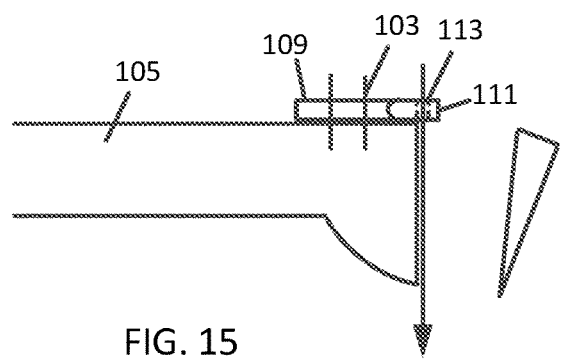

In another embodiment, the cutting block can be a stand-alone apparatus unlike the shims that are designed to attach to existing instrumentation. The cutting block can have cupped and/or rounded distal contact points as described above or may use the shims described as above. This configuration can allow the surgeon to position the block on the femur using an intramedullary rod for flexion and extension alignment. The cutting block can be locked in a desired position by a series of pins to the femur through a number of options for pinning which pass through the block in a parallel fashion in such a way as to allow the block to be moved proximally in 1 mm incremental steps but also rotated about its axis to increase or decrease varus valgus alignment. For example, with reference to FIG. 3, a block 107 can have radially arranged pin holes 123. In the illustrated embodiment, only one set of pin holes 123 is shown. However, other pin hole 123 patterns are possible and might be optimal. The block 107 can have sharp elements on the bone facing side, which can penetrate the surface of the bone to discourage motion of the block 107 at the time of pinning and bone cutting. The block 107 can have the ability to adjust the varus/valgus flexion extension angle of the captured guide slot on the block 107 independently of the pins and without adjusting or removing the pins. With reference to FIG. 2, the block 107 can lock the cutting blade slot 113 in its new position. The locking mechanism is not shown. However, any known locking mechanisms can be used. The cutting guide blade slot 113 may have a metal lined and be made of plastic or metal or any other suitable material.
Tibial Cut Once the femur has been cut as described above with reference to FIGS. 7-10, the inventive system can be used to cut the tibia. The tibial cutting system can have several key features. In an embodiment with reference to FIG. 11, a tension device 167 can be placed between the tibia 105 and the femur 165 and a tension force can be applied to separate the tibia 105 from the femur 165. While in the tensioned state, a jig 163 can be attached to the block positioner 109 on the femur 165 and a block positioner 109 can be placed on the tibia 105. In an embodiment, the pin guide 127 can be placed in the block positioner 109 as shown in FIG. 5. With reference to FIG. 13, pins 103 can be placed through pin holes in the block positioner 109 on the tibia 105 and the jig can be removed. With reference to FIG. 14, a cutting block 111 can be attached to the block positioner 109. The cutting block 111 can have a provisional guide, which allows placement of the pins 103 that will hold the tibial cutting block 111 in place relative to the tibia 105. The cutting block 111 also has a blade slot 113. With reference to FIG. 15, a cutting blade can be placed through the blade slot 113 to remove a proximal portion of the tibia 105.

As described above with reference to FIGS. 11-15, the position of the tibial cutting block can be directly referenced from the femur, not the tibia or the tibia axis. The cut is referenced from the femoral cuts and uses the femoral cutting blocks as guides. The cutting block allows for the antior to posterior (AP) cut (slope) of the cut to vary. The cutting block also allows the actual tibial cut to be accurately made using the previously placed pins to hold the block in place. The cutting block can also provide recutting guides in a situation where the knee is not balance and alignment of the tibia and femur needs to be changed after the block is pinned to the tibia through a hinged cutting slot.

The pin holes can be designed to allow the blocks to be re-positioned in varus/valgus as needed. The blocks can be pinned directly from the femur block, or as an option the femur block can be used to place pins in the femur. The femur block can then be removed and another block can slide over these inserted pins. If the distal cutting block is not used and a shim is attached to the native instruments instead, then the connection between the tibial cutting block and the native block can occur through a right angle attachment that has inserts in the cutting slot of both blocks and holds both at a fixed distance and angle.
Provisional Pin Positioning Blocks.

In other embodiments, the placement of the tibial cutting block can be performed with specific process steps. Rather than using an extramedullary or intramedullary tibial referencing alignment jig, the tibial cutting block can be positioned using the distal femoral cut as the reference point.
Guided Tibial Cut in Extension:

Following the removal of the distal femoral bone resections and osteophytes, the tibial resection guide or pin placement guide can be placed in full extension to the distal femoral cutting block by means of a connector or if the hinged connector is used, by extending the hinge to 180 degrees. Laminar spreaders or spacers can be placed on both the medial and lateral side of the knee joint and equal tension is placed across the joint. The tibial cutting block or pin may be positioned so as to ensure a perfect amount of bone resection to enable/create a rectangular space in extension that is large enough to allow the insertion of the final femoral and tibial components including a polyethelene insert. There may be more than one connecting rod of different lengths to accommodate larger/smaller defects or implant design variations. In an embodiment, two metal blades can be passed through a different guide and into the posterior condylar cutting slots on the 4 in 1 femoral component. This provisional positioning block can allow the placement of two pins in the anterior tibia the position of which is therefore referenced from the posterior condylar cuts. These two pins will be used to hold the tibial cutting block in place. The cutting plane defined by the pin holes may not create a perfectly rectangular flexion gap but rather an asymmetric gap, wider laterally than medially by approximately 2 degrees. Once the femur cuts are completed, the tibia is translated anteriorly using standard techniques and osteophytes are removed prior to using the previously positioned tibial pins for implant placement.

The described technique can also be used with the knee in extension and using the distal cutting block's slots as references as long as all osteophytes have been removed and laminar spreaders (or wedges—see below) have been inserted to place the collateral ligaments in tension. If the femoral cuts have been completed, a horseshoe shaped block can be inserted with convex cupped surfaces roughly 8-9 mm thick between the femur and the uncut tibia in extension. Shims can be used to tension the collateral ligaments. Two pin holes on this block can then guide the placement of the pins into the tibia. In this example, the position of the pins should be parallel to the distal femoral cut when the collaterals are tensioned.

Tibial Cutting Block

The final cutting block can now be placed on the two previously placed pins and adjustments made. This block can be adjusted once it has been pinned in position or once the pins are seated and the block is slid over the pins and the resection height is adjusted. Further adjustments in the varus and valgus plane can be performed by selecting different holes in the block. In the flexion extension planes, the block's position can be adjusted (and to a lesser degree the rotational plane) by means of the universal joint which can be locked and unlocked by means of a central screw or similar mechanism that locks and unlocks the block. Once positioned satisfactorily, it is locked into a position and a third pin is placed prior to cutting the tibia. A hinged and lockable cutting block slot is thus the slot itself which by because it is hinged can be positioned in different planes of flexion/extension relative to the rest of the block. If the resection is not satisfactory or does not provide adequate balance, the block can be loosened and repositioned without removing the pins. In an embodiment, recutting blocks can be provided that allow a change in the valgus or varus cut on the tibia and/or the flexion or extension of the cut if the degrees of freedom in the tibial guide do not allow the cut to be adequately balanced.

The blocks illustrated in the figures are designed to show the variable angle options. However, solid, non-mobile blocks may be used to achieve the same outcomes. When performing kinematically-aligned TKA using the described tools, the surgeon can more easily align the femoral and tibial components parallel or perpendicular to the kinematic axes, which restores the natural joint lines. Restoring the natural joint lines aligns the limb and stabilizes the knee without releasing the collateral ligaments, retinacular ligaments, and posterior cruciate ligament. Kinematically aligned TKA results in better patient satisfaction and function, and better flexion than mechanically-aligned TKA, because mechanically aligned TKA changes the angle and level of the joint line from normal.

Technique for Flexion Gap Cutting Blocks

In other embodiments, the present invention can include techniques for creating kinematic tibial cuts with the knee in flexion and not in extension as described in the prior embodiments. These embodiments also solve the primary problem of producing a reproducible tibial cut that creates a balanced knee during TKA. The described methods are not limited to achieving cuts consistent with kinematic alignment as the cutting blocks herein described can be used in any situation where the flexion gaps need to be balanced to the femoral gaps by referencing from the posterior femoral condylar cuts. In other words, while the following technique was designed to create kinematically aligned cuts and gaps, it can be used to create standard balanced gaps as well. An important concept is the idea that rather than creating tibial and femoral cuts that are independent of each other and subsequently balanced through either soft tissue releases or bone cuts, the technique and instruments herein described link the cutting blocks for the tibia to the blocks used to make the femoral cuts while they are still in situ. That is, the tibial cuts can be made by mechanically linking the positioning of the tibial cutting guide to a traditional "4 in 1" cutting block on the proximal femur while the latter is still attached to the femur, no chamfer cuts have been made, and the knee is flexed. This creates tibial cuts that are linked to the posterior femoral geometry in flexion (regardless of how it was created in terms of alignment philosophy) and thus produce accurate resections for that particular alignment. When the process herein described is used, the resulting TKA component positioning can produce well balanced knees very reliably with minimal if any need for surgeon judgment or prior experience, particularly with cruciate retaining total knee techniques.

Surgical Technique for Cutting the Tibia in Flexion Using Linked Guides.

The distal femoral cut can be performed using either routine cutting blocks (for the purpose of this document, "routine" or "standard" cutting blocks refers to the cutting blocks that are supplied by the manufacturer of the implant for the purpose of making the bone cuts necessary for component placement) or the previously described cutting blocks and shims. With the distal femoral cut completed, the thickness of the resected bone can be checked for accuracy. For example, the total thickness of resected bone must equal to the thickness of the component minus the kirf (the saw thickness) minus the thickness of the lost cartilage (if any). If these resections are not accurate, then appropriate corrective measures are taken to avoid inaccurate component alignment. All peripheral femoral and tibial osteophytes that may impinge on collaterals are next removed from the femur and tibia. The femur is then sized using the implant system's standard posterior referencing jig. The femoral component's rotation is set at zero degrees relative to the posterior condylar axis (for a kinematically aligned knee) or in the surgeon's preferred position for any other kind of alignment technique and this is marked with drill holes or pins based on the standard surgical technique.

An appropriate size "4 in 1" chamfer cutting block can then be secured to the distal femur per the company technique. No further cuts are made at this point. If necessary, the gap wedges (see description) can now be inserted in the worn joint space(s) between the tibia and the posterior femoral condyles with the goal of tightening the flexion gap if the gap is loose (with the knee at 90 of flexion).

Figure 32:
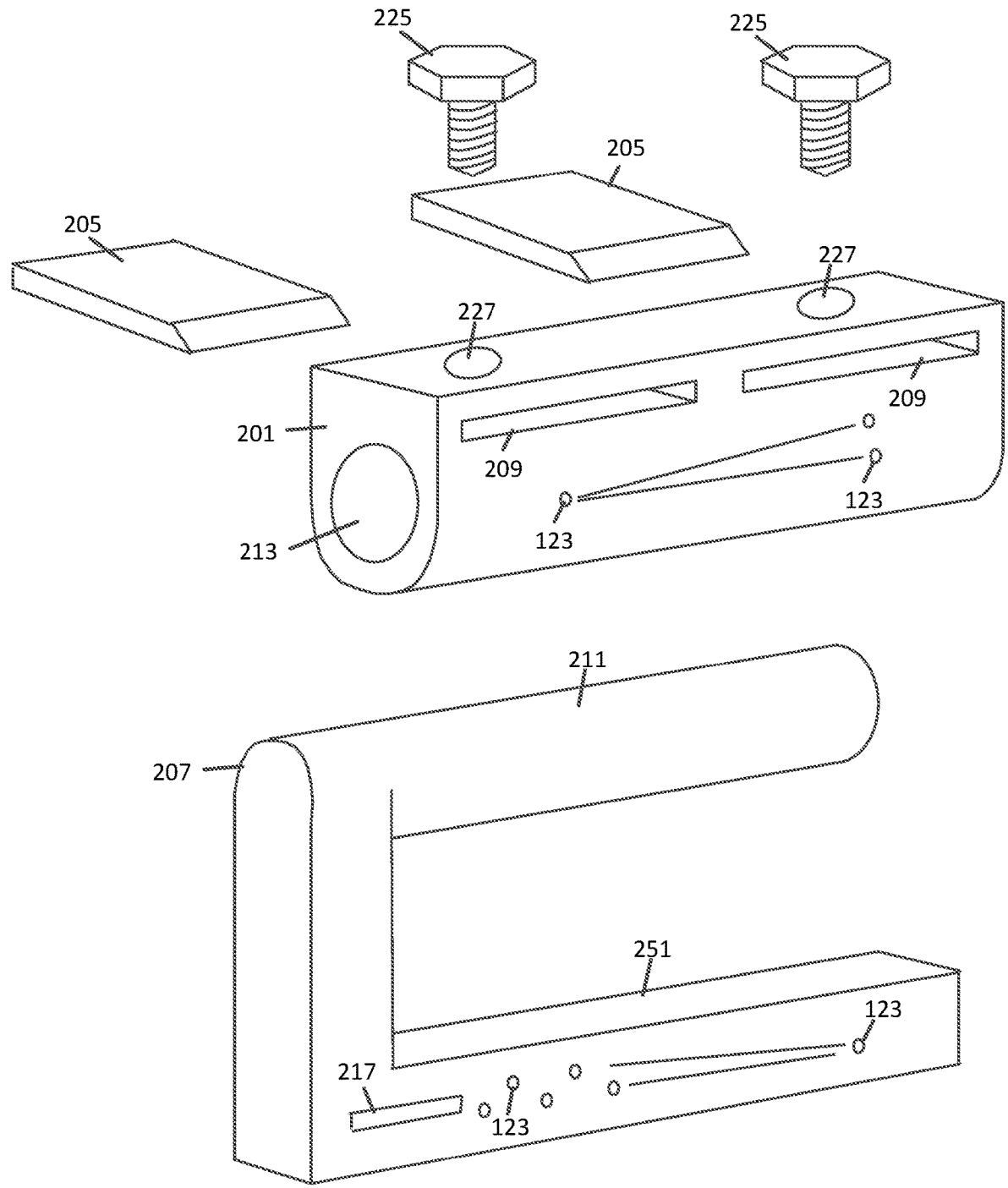
FIG. 32 illustrates an exploded view of an embodiment of a gap guide system components.

With reference to FIG. 32, a gap guide body 201 and components are illustrated. The wedged blades 205 of the pin guide body 201 are inserted into the cutting slots 207 of the "4 in 1" cutting jig intended for the posterior condylar cuts until the pin guide body 201 is stable and engaged to the "4 in 1" cutting block. The rotating targeting guide (RTG) 207 is then assembled to the body 201 from medial to lateral until the targeting device is centered approximately over the medial third of the tibial tubercle using an etched mark on the guide body 201 as a reference point. A cylindrical portion 211 of the RTG 207 can be placed in an RTG hole 213 in the body 201 and rotated to a designated rotation. Lock screws 225 can be threaded into holes 227. The screws 225 can press against the cylindrical portions 211 of the RTG 207 to lock the RTG 207 at a designated rotation. The screws can be tightened onto the RTG 207 to prevent it from sliding out of the RTG hole 213. The guide body 201 can also include a wing slot 217 and a plurality of pin holes 123. The targeting device 207 is then rotated on its axis until the pin holes 123 are angled to match the plane of the tibial slope of the tibia.

Figure 33:
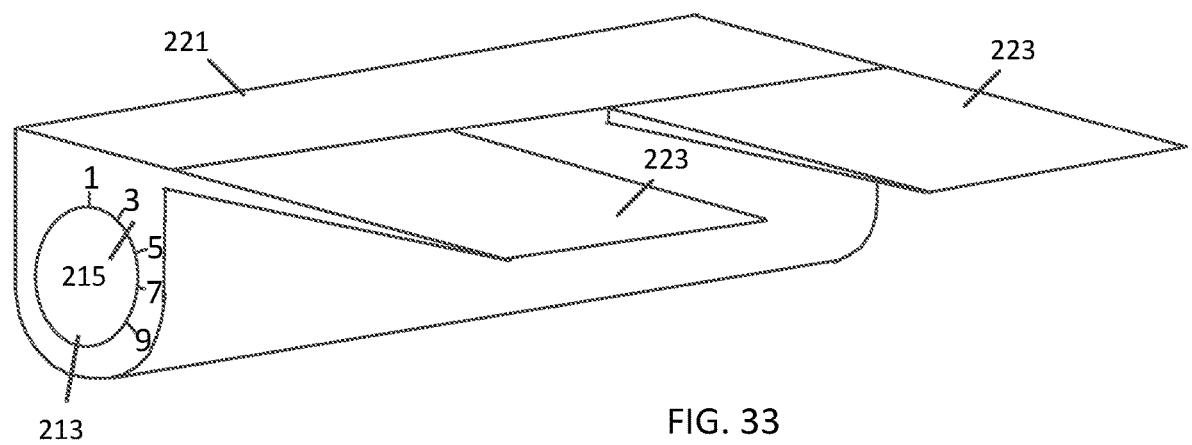
FIG. 33 illustrates a top perspective view of an embodiment of a guide body.
Figure 34:
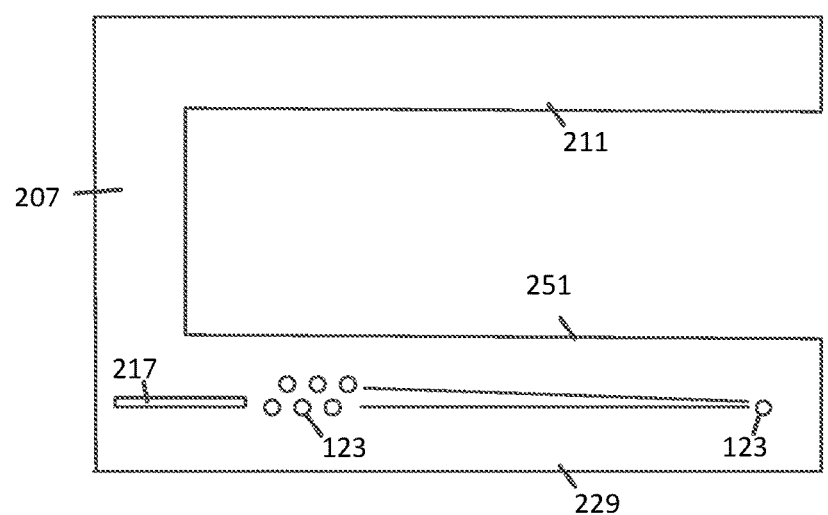
FIG. 34 illustrates a front view of an embodiment of a rotating targeting guide.

With reference to FIG. 33, in an embodiment, the guide body 201 can have rotation markings 215 and fixed blades 223. In this example, the rotation markings 215 numbered 1 to 9. When an RTG is inserted into the RTG hole 213, the extent of the RTG rotation, or slope, can be checked from the rotation marks 215 which can be etched or otherwise formed on the side of the pin guide body 221. With reference to FIG. 34 a side view of an RTG 229 is illustrated. The RTG 229 can have one or two rows of pin holes 123 which can form different relative angles across the length of the RTG 229.

Figure 35:
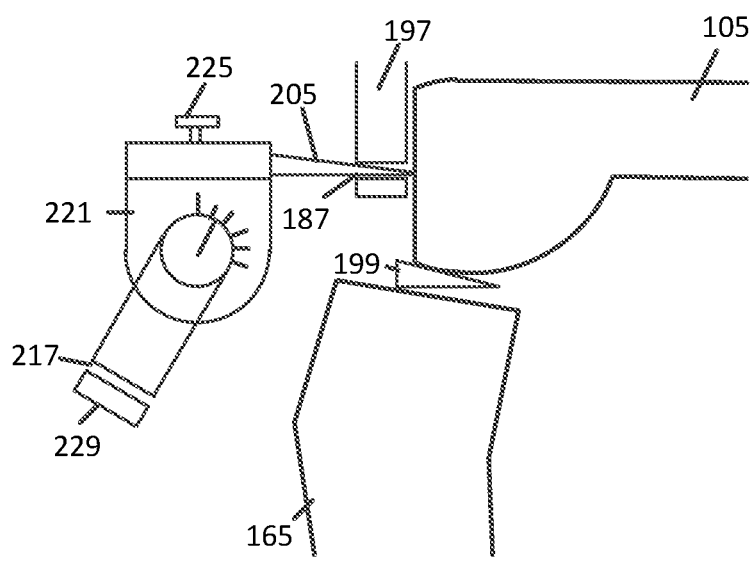
FIG. 35 illustrates a side view of an embodiment of a guide body and rotating targeting guide.

With reference to FIG. 35, blade 205 of the guide body 221 is placed through the posterior chamfer cutting slot 187 of the 4-in-1 cutting block 197 that has, at this point, been locked to the femur 165. The blade 205 can be secured to the guide body 221 and positioned about 9 mm up from the posterior most aspect of the post femoral condyle. The RTG 229 can be positioned and locked in place with screws 225. The wedge 199 is used to separate (tension) the femur 165 and the tibia 105 and ensure that the gap between the surfaces is under tension. In other embodiments, the wedge 199 can be replaced by a spring mechanism as well or a laminar spreader.

Figure 37:
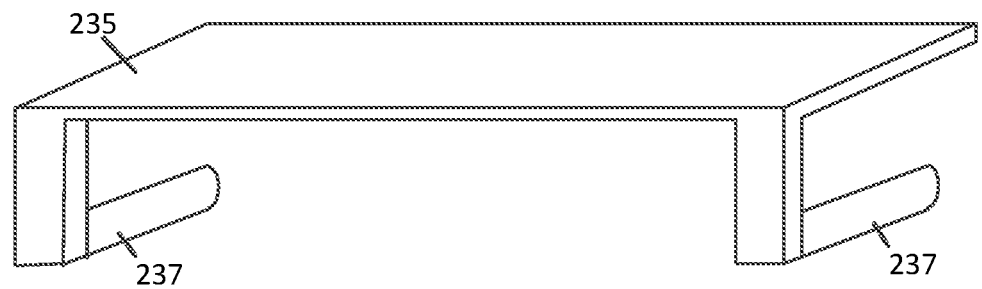
FIG. 37 illustrates an embodiment of a saw blade capture.

While maintaining the knee in flexion, if the surgeon wishes to create a tibial bone cut using the instruments herein described, the top of the guide body can be used as the cutting surface. The surgeon can simply slide the pin guide body over the pins already in place in the tibia using the zero degree pin holes (or the 2 degree pin holes as needed). The surgeon can then assemble the saw blade capture to the body, places a locking pin through the body into the tibia as needed, and performs the cut. An embodiment of a saw blade capture 235 is illustrated in FIG. 37.

As mentioned above, unless the pins have already placed through the kinematic pin holes in an earlier step, if the surgeon wishes to perform a kinematic cut, with approximately 2 mm greater laxity laterally than medially, they would choose the 2 degree holes in the pin guide body through which to slide the pins. The medial hole being the same one as the zero degree cut and the lateral one being in 2 degree less varus than the parallel—or zero degree—pin holes. The surgeon can use of the 2-degree lateral pin hole to place the cutting block in 2 degrees less varus than the zero degree lateral pin hole. This can be done to create a 2 mm gap that is laterally greater than medially and assumes that each degree of varus of the lateral pin hole relative to the medial pin hole and creates approximately a 1 mm>difference in the lateral resection height.

Following the completion of the tibial cut, the joint can be cleared of residual soft tissues (menisci and scar tissue) and checked for balance in flexion and extension using the surgeon's preferred method. For example: spacer blocks or tensioners can be used to perform this check. In the unlikely event that the knee is not adequately balanced the surgeon can perform additional steps. If the surgeon wishes to cut 2 mm more bone from both sides of the tibia, they can use either the +2, 3 or 4 mm holes on the body to lower the cutting plane and then subsequently cut the extra bone. If the surgeon needs to cut in 2 more degrees of varus (or less) the surgeon can again use the pin guide body's pin holes to further increase or decrease the amount of varus or valgus. Having achieved balanced gaps, bone preparation continues according to standard guidelines for the component being implanted.

The inventive gap guide block assembly can have a plurality of device components. For example, the Tibial cutting guide components can include: a pin guide body (body), pin guide body blades (blades), pin guide body wing (wing), a rotating targeting guide (RTG), a saw blade capture (capture), gap tension wedges (wedges), and a pin repositioning guide. All components can be designed as single use or multi use devices.

Gap Guide Body

With reference to FIG. 33, the gap guide body 221 can be a monolithic or a modular structure. The upper surface of the body 221 can be flat and the lower surface can be round on the bottom to match the radius of curvature of a RTG. This bottom surface of the body 221 can be smooth to allow for complete rotating freedom of the RTG, or, alternatively, the bottom surface can be notched with an engagement pin for ratcheting between a plurality of predetermined fixed rotational positions. The long axis of the gap guide body 221 can have a cylindrical hole 213 for the RTG. In an embodiment, the RTG can be coupled to the body 221 with the cylindrical portion of the RTG placed in the cylindrical hole 213. In other embodiments, any other connection can be used to coupled the RTG to the body 221 that provides variable positioning of the pin guide relative to the targeting device. The slot 213 can have marks 215 to denote the extent of angulation of the RTG from a neutral position. In an embodiment as shown in FIG. 33, the blades 223 can be part of an integrated structure that is attached to the body 221 forming a homogeneous monolithic component. The blades 223 in this embodiment can thus extend only a fixed distance from the body 221.

In a modular embodiment with reference to FIG. 32, the blades 205 can be separate from the body 201 and the blades 205 can pass through slots 209 in the body 201. The blades 205 in this embodiment can be adjustable and extend a variable distance from the body 201. The blades 205 can be made of metal or plastic or combination of suitable materials. The blades 205 can be tapered to engage the slots 209 in the distal femoral cutting block or slide freely within the slots 209. The blade 205 can be made strong enough to not flex and be approximately 1.2 mm thick to match the thickness of most surgical blades (and therefore the slot thickness of standard "4 in 1" cutting blocks). The blades 205 may have an "I beam" geometry or surface configuration to allow for stiffening of the blade 205.

With reference to FIG. 32, the blade slot(s) 209 for the blades 223 can be placed along the longitudinal axis of the body 201. The slot(s) 209 can be a single slot, double slots, ridged or smooth slots. The slot(s) 209 may also have a locking device to the body 201 which can be a screw 225 or other compression device or lock the slot(s) 209 by wedging them into the slot(s) 209.

Figure 38:
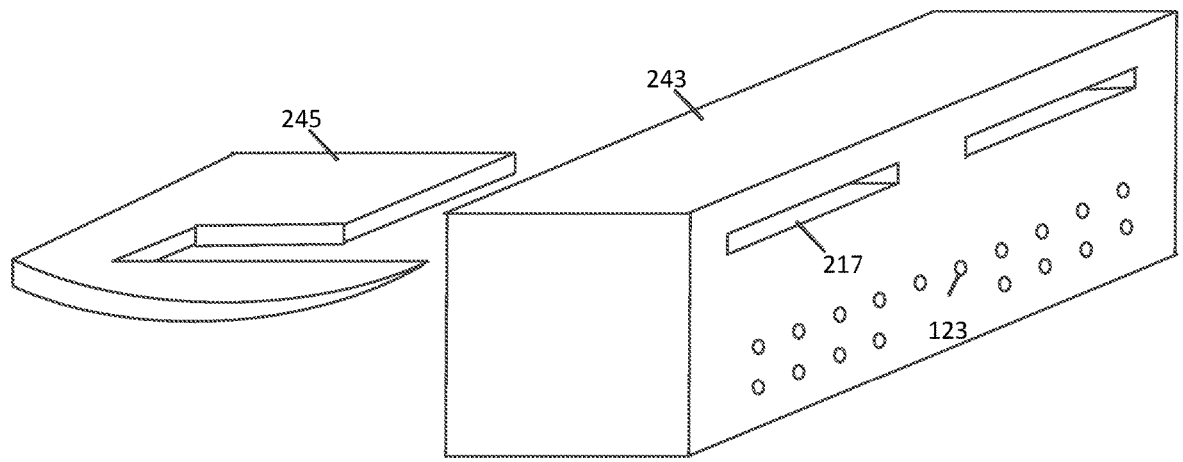
FIG. 38 illustrates an embodiment of a wing and guide body.

With reference to FIG. 38, the wing slot 217 in the guide body can be used by a surgeon to check to determine if the slope is accurate. A wing 245 can slide into the slots 217 of the pin guide body 243 and enable judging the slope of the tibial cut when the body 243 is used as a cutting block. If the pin guide body 243 is also used as a cutting block for the tibial cut, the wing 245 can be used to visualize the plane of the tibial cut. Once the block 243 is in place and prior to securing the block 243 to the tibia by means of headed screws, the wing 245 is placed into the cutting slot 217 to show the approximate trajectory of the saw blade. The wing 245 can be made of plastic, metal or any other suitable material. Pin holes 123 can be formed in the pin guide body 243.

Figure 39:
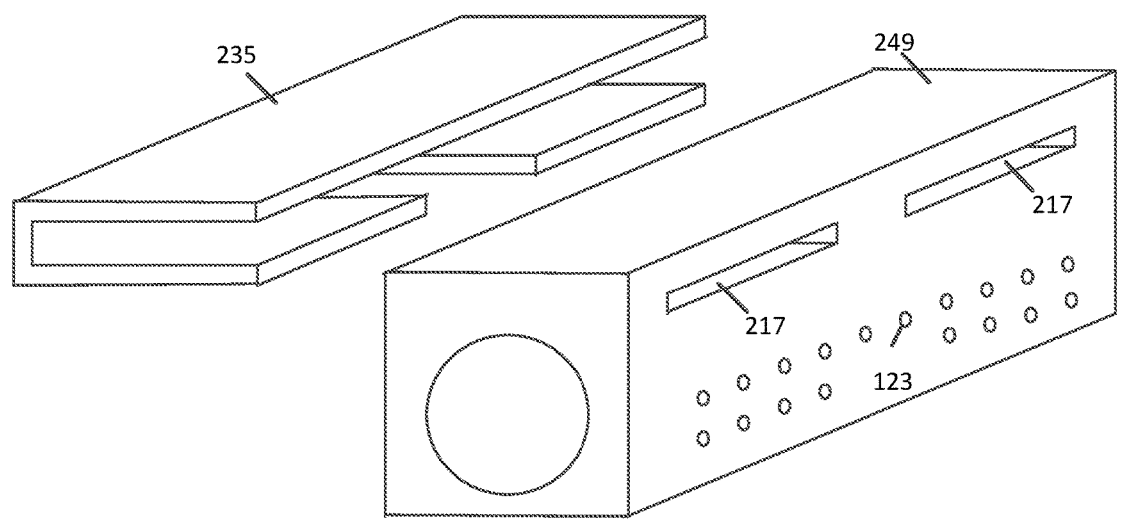
FIG. 39 illustrates an embodiment of a saw blade capture and rotating targeting guide.

With reference to FIG. 39, in an embodiment the cutting block body 249 can include a saw blade capture mechanism 235, which allows the body 249 to be used as the saw blade's cutting guide for the tibial cut. The capture mechanism 235 can be the width and depth of the body 249 and may keep the saw on the same plane as the cutting block body 249. The blade capture mechanism 235 can have lateral captures to prevent the saw from slipping outside the cutting block of the body 249. The capture mechanism 235 can engage the blades in the blade slots 217 in the cutting block 249. The capture mechanism 235 may also or alternatively engage in separate holes in the block 249. The capture mechanism 235 can engage the blade through the RTG. Pin holes 123 can be formed in the body 249.

With reference to FIG. 32, the pin holes 123 in the illustrated embodiments of the body 201 can provide numerous functions. For example, in different embodiments, the pin holes 123 can be used for positioning the body 201 so that the body 201 can be used as a tibial cutting guide. In an embodiment, the tibial cut is 10 mm below surface of the tibia. The pin holes 123 can also be used for increasing or decreasing the amount of bone resection Varus or valgus, Cephalad to Caudal simply by changing the holes 123 in the body 201 are selected for the previously placed tibial pins. Further, any of the pin holes 123 that are not occupied can be used for locking the body 201 in a desired position and preventing it from sliding in or out of place during sawing.

The pin holes 123 in the body 201 can be arranged in multiple sets of different design configurations. For example, zero degree pin holes 123 can be parallel to the posterior femoral condylar cut regardless of surgical technique. Two degree pin holes 123 can have the same medial pin hole 123 as the zero degree pin holes 123, however the lateral pin hole 123 can be placed along a line extending from the medial pin hole 123 laterally at an angle that is 2 degrees less varus than the zero degree pin hole 123 plane. A third pin hole 123 can be along a line that is in 4 degrees less varus and a fourth pin hole 123 can be along a line that is in 6 degrees of varus. Each lateral pin hole 123 would be a fixed distance from the medial pin hole 123. In another embodiment, a series of pin holes 123 can be placed along each axis to match pin hole 123 distances used my multiple manufactures in case the surgeon wishes to use a specific manufacturer's tibial cutting block rather than the body 201 to make the tibial cut. The body 201 may have +2 mm pin holes 123 that are 2 mm above zero-degree pin holes 123. The +2 mm pin holes 123 may be offset 1 to 2 mm to allow pin placement in the new bone.

Figure 36:
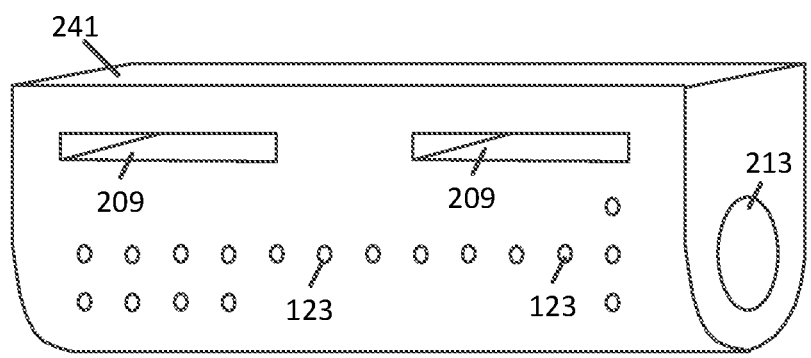
FIG. 36 illustrates a front view of an embodiment of a repositioning block.
Figure 40:
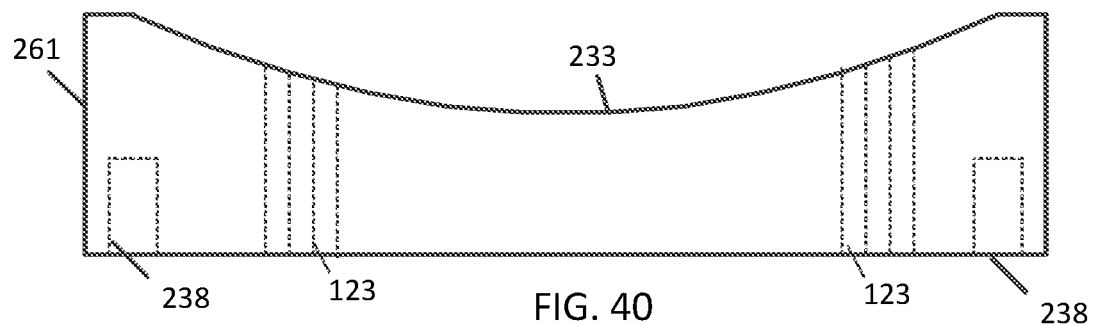
FIG. 40 illustrates a top view of an embodiment of a cutting block body.
Figure 41:
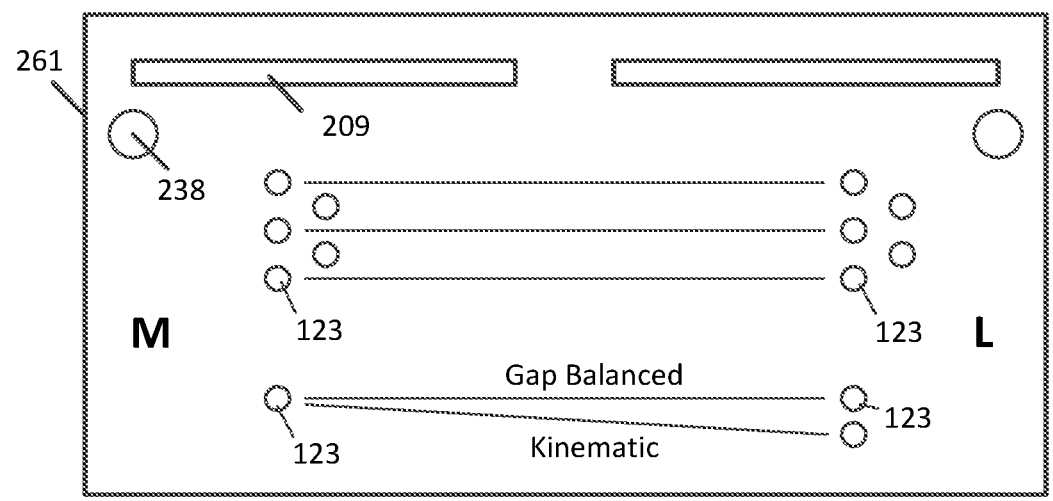
FIG. 41 illustrates a front view of an embodiment of a cutting block body.

FIG. 40 illustrates a top view and FIG. 41 illustrates a side view of another embodiment of a cutting block body 261 that may be a single monolithic block with the slots 209 for the blades but without a longitudinal hole or other capture for an RPG. Rather, the block body 261 has a set of tibial pin holes 123 that are drilled directly into the body 261 in the Anterior Posterior plane at a 5-degree angle/slope from the plane of the blades. These are the angled tibial pin holes 123 and there are two options: one pin holes 123 parallel to the blades and two pin holes 123 offset by 2 degrees to allow for kinematic alignment. Two or more pins 103 can be placed into the tibia 105 using the neutral pin holes 123 in the pin guide body 275 if mechanical alignment is desired or the 2 degree slots for kinematic alignment. The neutral pin holes 123 can position the pins 103 parallel to the posterior condylar axis, while the oblique pin holes 123 can place the pins 103 in such a way as to create a trapezoidal gap that is 2 mm wider on the lateral side. This choice would be used in kinematic alignment, where a guide body as shown in FIG. 36 can be used. The entire guide body and RPG can then be removed leaving the tibial guide pins 103 in place. The femoral chamfer cuts can be completed and the femoral bone segments can be removed.

To further change the anterio-posterior slope (more or less than 5 degrees), the surgeon simply flexes and extends the knee and changes the position of the tibia. The angled tibial pin holes 123 are so positioned from the level of the blades as to allow the pins to establish an approximately 10 mm resection from the top of the tibia. The opposite sides of the body 261 can be marked with "M" to designated the medial side and "L" to designate the lateral side. A rear surface 233 of the body 261 can have a concave curvature.

In an embodiment, these pin holes 123 can be approximately 18 mm from the level of the blade slots 209. The body 261 itself has another set of pin holes 123 set apart the same distance as the tibial pin angled guide holes, that allow the top of the body 261 to be used as a tibial cutting surface. These pin holes 123 allow the body 261 to be positioned to create a tibial cut that is 9-13 mm in thickness in 1 mm increments. For example, the upper pin holes 123 can be 9 mm below the blade slots 209 and the lower pin holes 123 can be 13 mm below the blade slots 209.

A blade capture can also be available as is a recut guide that allows an angle of 1 to 2 degrees from varus of valgus to be cut with the medial pin being "the fixed point" of rotation (see below, also FIG. 36). The blade capture can include cutting block capture slots 235 which can be secured to a saw blade capture. FIG. 37 illustrates an embodiment of a saw blade capture 235 which has legs 237 which can be cylindrical in shape. The legs 237 can be placed in the capture slots 238 in the cutting block body 261 to secure the saw blade capture 235 to the cutting block body 261 shown in FIGS. 40 and 41.

Rotating Targeting Guide (RTG) With reference to FIG. 32, the RTG 207 can be designed with pin holes 123 to allow placement of the tibial cutting block pins into the proximal tibia in a position coplanar to the plane of the femoral posterior condylar cuts with the tibia in flexion. The pins positioned with the aid of the RTG 207 allow a minimum fixed 8 mm bone resection from the tibia. The RTG 207 has a rotating rod 211 rigidly connected to the pin boom 251 (FIG. 32). The RTG 207 can be made of plastic, metal, other suitable materials or combination of materials. The technique for pin placement may require that the posterior gaps are under normal soft tissue tension and therefore the use of a wedge or similar tensioning device can be recommended if there is either tibial bone loss or cartilage loss.

A rotating cylindrical rod 211 can be used to attach the RTG 207 to the hole 213 in the body 201 so that the RTG 207 can only move or rotate in only one plane. Alternatively, the RTG 207 can also be connected to the body 201 through a different coupling mechanisms such as a longitudinal slot or any other capture method or mechanism that allows only one plane of motion. The rotating rod 311 motion within the body 201 can be smooth or indexed in fixed rotational increments. For example, with reference to FIG. 33, the indexed rotation can correspond to markings 215 on the body 221 so that the RTG can be easily positioned in alignment with any of the markings 215. In an embodiments, the RTG or the gap guide body 221 can have a locking mechanism to stop the cylindrical rod and the RTG from rotating. The locking mechanism can be released to allow the RTG to move freely within the RTG hole 213.

With reference to FIG. 32 and FIG. 34 which illustrates a side view of the RTG 207, the boom 251 can include pin holes 123 through the thickness of the boom 251 that allow placement of the pins such that the body 201, when used as a cutting block, or any other cutting block that uses the pins for placement, produces a cut in the tibia that is at an 8 mm (first row of pin holes) or 10 mm (second row) resection height from the upper surface of the boom 251. The boom 251 can have a flat surface to allow it to be used as a cutting block. In an embodiment, the boom 251 may have a saw blade capture guide that can be made of metal or plastic or both. In different embodiments the boom 251 may be linked to the body or the RTG through clips, screws, short pins, elastic or blades.

In an embodiment, the pin hole placement in the boom 251 can be configured and designed to match the pin hole diameter and spacing of a specific surgical instrument set so that the pins placed in the tibia can be used with the "Standard" cutting blocks from a specific implant manufacturer.

Repositioning Block.

In the event that using the guide body as a cutting block is deemed too challenging, the surgeon can use a repositioning block as a pin repositioning guide. FIG. 36 illustrates an embodiment of a repositioning block 241. The repositioning block 241 can have the same pin hole 123, an RTG hole 213 and blade slots 209 configuration as described for the guide body. However, the repositioning block 241 may not have any of the other slots or holes thus making pin hole 123 selection easier. The repositioning block 241 can have various possible geometries such as: a rectangular shape, shaped to match the proximal femur and have a saw guide and or capture.

Figure 42:
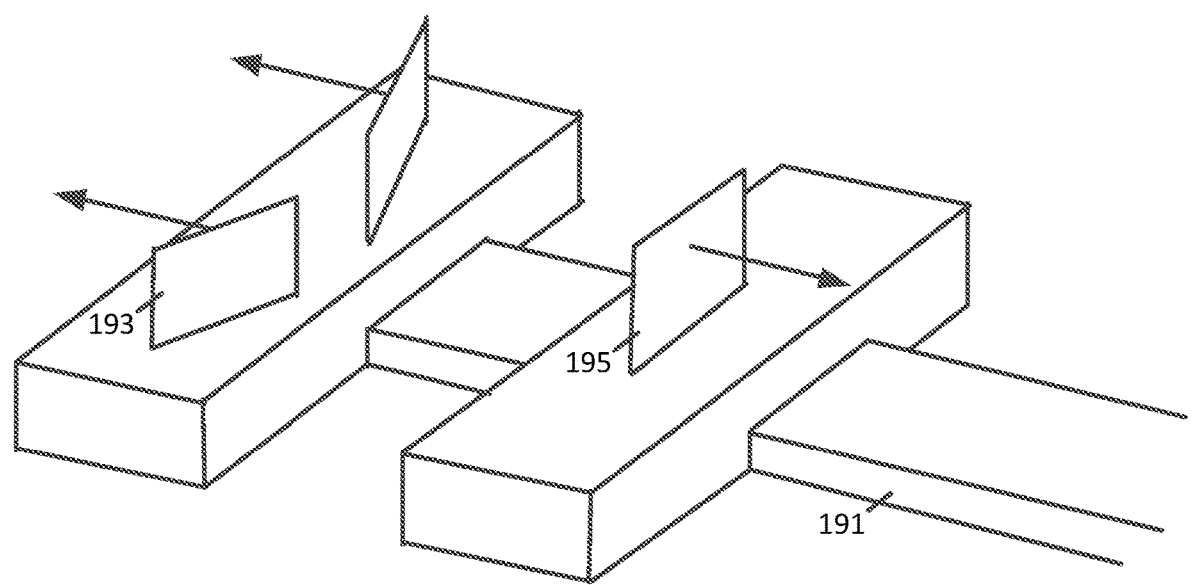
FIG. 42 illustrates an embodiment of a tibia and femur separation tool.
Figure 43:
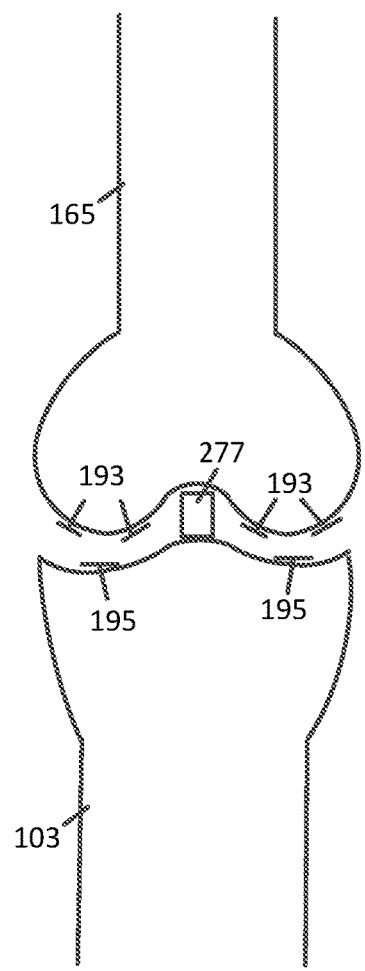
FIG. 43 illustrates an embodiment of a separation tool used with a tibia and femur.

It can be desirable to tension the tibia and femur to separate the bones and then make cuts to the bone(s) while under tension. With reference to FIG. 42, a top perspective view of an embodiment of a tensioner 191 is illustrated. The tensioner 191 can include one or more femur blades 193 and one or more tibia blades 195. The alignment of the femur blades 193 and tibia blades 195 can be variable so the femur and tibia are in the desired alignment when tensioned. With reference to FIG. 43, a front view of the tibia 103 and femur 165 are illustrated. The tensioner can be placed against the tibia 103 and femur 165 with the tibia blades 195 against the proximal end of the tibia 103 and the femur blades 193 against the distal end of the femur 165. The tensioner can be actuated to separate the femur blades 193 and tibia blades 195. In this tensioned position, the femur 165 and/or tibia 103 can be cut as described above.

In an embodiment, a gap tension wedge 177 can be placed between the femur 165 and the tibia 105 to help expand and maintain the gap between the tibia 103 and femur 165. For example, the tensioner can be used to expand the gap between the tibia 103 and femur 165. At the desired tension, the gap tension wedge 177 can be placed between the tibia 103 and femur 165 to maintain the gap distance. These gap tension wedges 177 can be used in other tensioning systems. For example, in some embodiments, the tibia and femur can be separated (tensioned) in extension using a wedge and a spacer.

Figure 44:
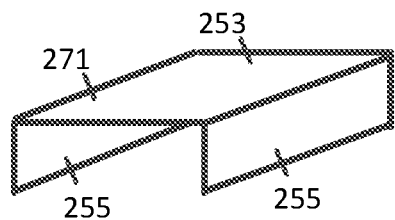
FIG. 44 illustrates a top perspective view of an embodiment of a spacer.
Figure 45:
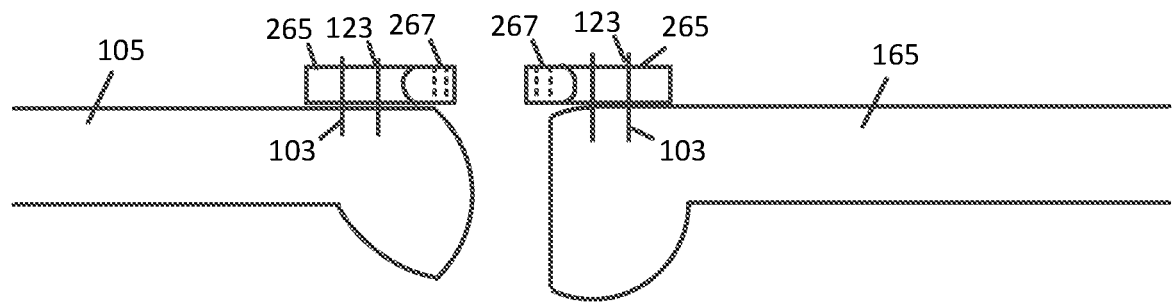
FIG. 45 illustrates a side view of a tibia and femur spacer system.
Figure 46:
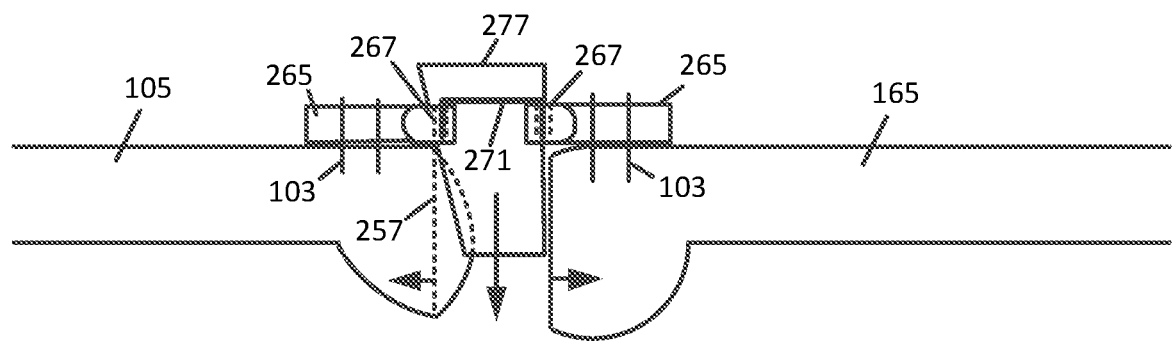
FIG. 46 illustrates a side view of a wedge used with a tibia and femur spacer system.

FIG. 44 illustrates an embodiment of a spacer 271 that can have two planar sections 255 that extend downward and a center body 253. The spacer 271 can be used with alignment devices attached to the tibia and femur. FIG. 45 illustrates a side view of an alignment device with pin guide bodies 265 attached to the femur 165 and tibia 105 with pins 103 placed through pin holes 123. In this example, the femur 165 has been cut and the cutting position of the tibia 105 is referenced from the femur 165. With reference to FIG. 46, a gap tension wedge 277 is placed between the tibia 105 and the femur 165. In this example, the gap tension wedge 277 can have a flat surface that slides along the cut surface of the femur 165 and an angled surface that slides against the tibia 105. When the tibia 105 and femur 165 are properly separated, the spacer 271 is placed into the slots 267 in the guide bodies 265. Once the spacer 271 is positioned, it can hold the tibia 105 and the femur 165 in the separated position. The tibia 105 can be cut as designated by the cutting line 257.

Figure 47:
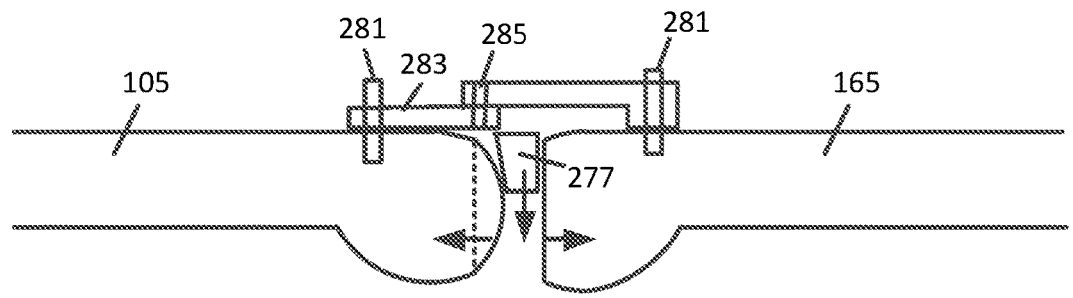
FIG. 47 illustrates an embodiment of a tibia and femur wedge separation system.

With reference to FIG. 47, yet another embodiment of a surgical tool for separating the tibia 105 and femur 165 is illustrated. In this embodiment, the tensioning and cutting guide tool 283 is coupled to the tibia 105 and femur 165 with bone pins 281 that are attached to the tool 283 and extend into the tibia 105 and femur 165. The movement of a gap tension wedge 277 can separate the tibia 105 and femur 165. The cutting guide tool 283 can control the separation and alignment of the tibia 105 and femur 165. When the tibia 105 and femur 165 are properly separated and aligned with the gap tension wedge 277, the tibia 105 can be cut with a cutting mechanism placed through the cutting slot 285.

Gap Tension Wedges.

Figure 48:
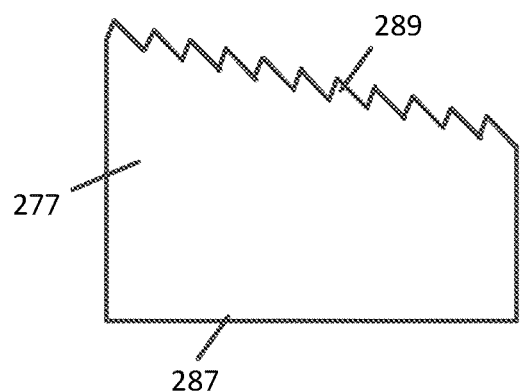
FIGS. 48-51 illustrate embodiments of wedges with friction surfaces.
Figure 49:
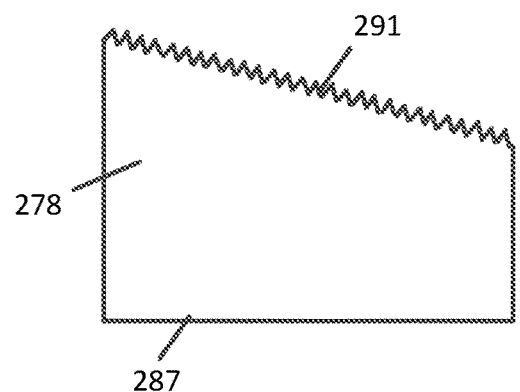
Figure 50:
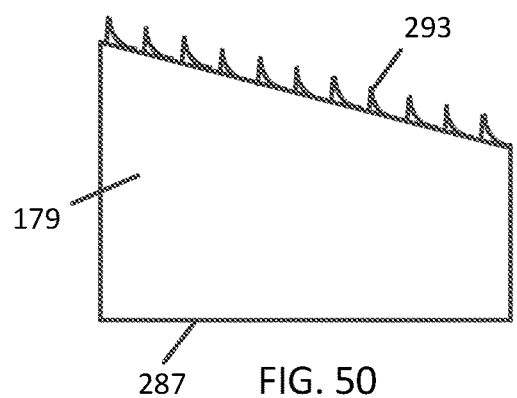
Figure 51:
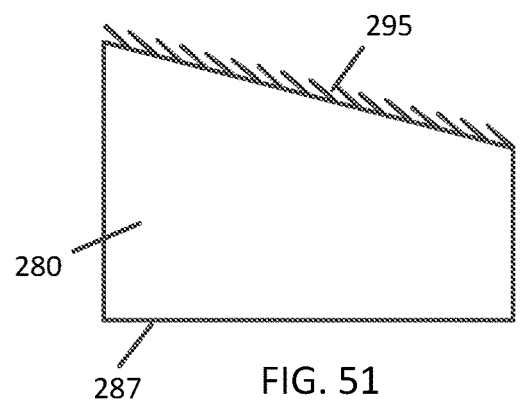

With reference to FIGS. 48-51, the gap tension wedges can be designed to open and stabilize the flexion gap medially or laterally in the presence of bone or cartilage loss. The wedges 277 may have various and different surface features and geometries. For example, in different embodiments, the wedges 277 can be: rough, ridged, barbed, smooth, tapered, rectangular and/or curved in any plane to match femoral or tibial curvature. In the illustrated examples, the gap tension wedges 277 can have surface features which allow them to be inserted between the femur and tibia to separate the femur and tibia but resist removal. With reference to FIG. 48, the wedge 277 has a smooth surface 287 and an angled surface that has a saw tooth surface texture 289. The wedge 277 can be inserted between the femur and tibia which apply a compression force against the smooth surface 287 and the textured surface 289 of the wedge 277. Thus, the textured surface 289 can have a non-uniform coefficient of friction with the bone. The insertion direction coefficient of friction can be lower than the removal direction coefficient of friction so the wedge 277 can be inserted but resists removal. FIG. 49 illustrates a wedge 278 having a finer toothed textured surface 291. FIG. 50 illustrates a wedge 279 having a curved barb textured surface 293 and FIG. 51 illustrates a wedge 280 having a protrusions surface 295 here the protrusions face the thicker portion of the wedge 280 that allow sliding in a direction that flattens the protrusions but resists movement in the opposite direction.

Figure 52:
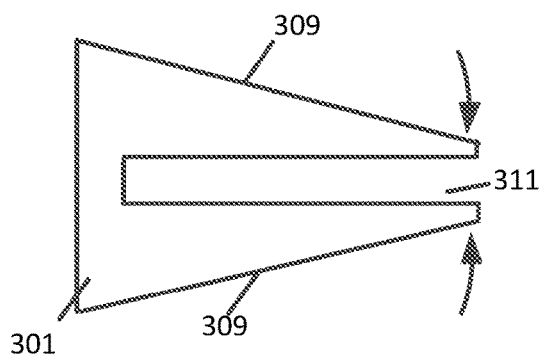
FIGS. 52-55 illustrate embodiments of compressible wedges.
Figure 53:
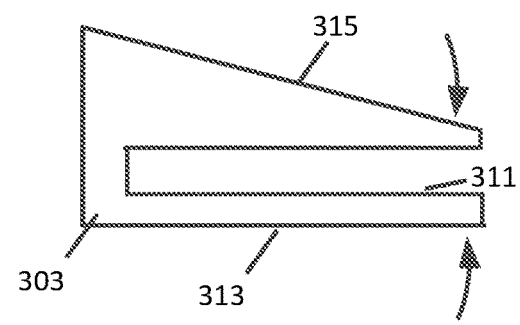
Figure 54:
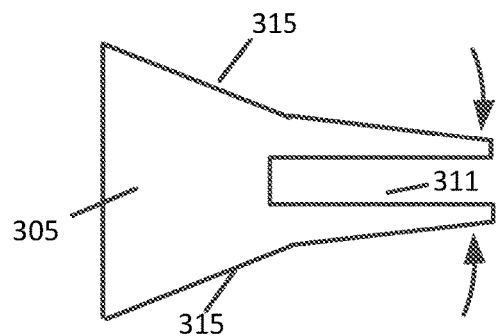
Figure 55:
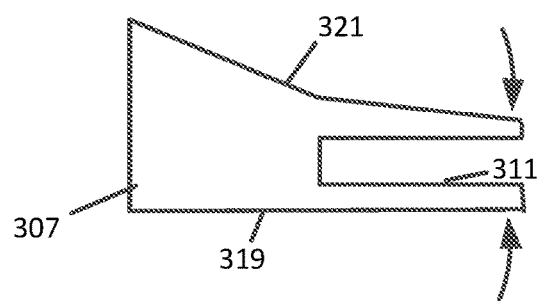

FIGS. 52-55 illustrate gap tension wedges that have simple geometric shapes. In other embodiments, the wedges have various different shapes that can provide functionality such as compressibility. A surgeon can select a wedge design based upon the patient's knee geometry. With reference to FIG. 52, a gap tension wedge 301 can have a more symmetric triangular shape with opposite siding surface sides 309 that are straight or planar and evenly tapered. The wedge 301 can also have a slot 311 which can allow the sides 309 to compress towards each other when the wedge is placed between the tibia and femur. With reference to FIG. 53, an embodiment of a wedge 303 having asymmetric straight side surfaces 313, 315 with a slot 311 that can allow the wedge 303 to compress. With reference to FIG. 54, an embodiment of the wedge 305 can a symmetric shape with variable angled side surfaces 315. In this embodiment, the wedge 305 can have a lower angle at the front portion and a sharper angle at the rear portion. The slot 311 in this embodiment only extends partially through the wedge 305 so that only the front portion can be compensable. With reference to FIG. 55, in an embodiment of the wedge 307 can have a straight surface 319 and a variable angled surface 321 with a slot 311 that only extends partially through the wedge 307. The wedges used with the present invention can be made of plastic, metal, any other suitable material or combination of materials. Their purpose is to act as opening wedges that place the collateral ligaments in tension in situations where there is bone or cartilage loss from either the femoral or tibial side.

The present disclosure, in various embodiments, includes components, and apparatus substantially as depicted and described herein, including various embodiments, sub-combinations, and subsets thereof. Those of skill in the art will understand how to make and use the present disclosure after understanding the present disclosure. The present disclosure, in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation. Rather, as the flowing claims reflect, inventive aspects lie in less than all features of any single foregoing disclosed embodiment.

What is claimed is:

1. A method for cutting a tibia comprising:
   providing a femur block positioner coupled to an alignment arm and a shim coupled to the alignment arm, wherein the shim has a concave surface;
   placing the concave surface of the shim on a distal end of a femur;
   securely attaching the femur block positioner to the femur while the concave surface of the shim is on the distal end of the femur;
   attaching a cutting block to the femur block positioner, the cutting block having a femur blade slot that is aligned with a cutting plane of the femur;
   cutting the femur using the femur blade slot to align a cutting tool;
   applying a tension force between the femur and a tibia;
   attaching to the femur block positioner a tibia cutting guide tool having a tibia blade slot; and
   cutting the tibia while the femur and the tibia are in tension.

2. The method of claim 1 further comprising:
   placing an intra-medullary rod in the distal end of the femur; and
   placing an end of the intra-medullary rod through an intra-medullary rod hole formed in the alignment arm.

3. The method of claim 1 further comprising:
   placing a pin through a pin hole in the femur block positioner and into the femur to attach the femur block positioner to the femur.

4. The method of claim 1 further comprising:
   removing the alignment arm and the shim from the femur block positioner before attaching the cutting block to the femur block positioner.

* * * * *